(12) United States Patent
Kim et al.

(10) Patent No.: US 10,889,819 B2
(45) Date of Patent: Jan. 12, 2021

(54) VISCERAL ADIPOSE TISSUE MACROPHAGE-TARGETED GENE/CARRIER COMPLEX FOR PREVENTING OR TREATING OBESITY-INDUCED TYPE II DIABETES

(71) Applicant: INDUSTRY-UNIVERSITY COOPERATION FOUNDATION HANYANG UNIVERSITY, Seoul (KR)

(72) Inventors: Yong-Hee Kim, Seoul (KR); Yoon Sung Song, Gyeonggi-do (KR); Seok-Beom Yong, Seoul (KR)

(73) Assignee: INDUSTRY-UNIVERSITY COOPERATION FOUNDATION HANYANG UNIVERSITY

( * ) Notice: Subject to any disclaimer, the term of this patent is extended or adjusted under 35 U.S.C. 154(b) by 0 days.

(21) Appl. No.: 16/370,259

(22) Filed: Mar. 29, 2019

(65) Prior Publication Data

US 2019/0300886 A1  Oct. 3, 2019

(30) Foreign Application Priority Data

Mar. 29, 2018  (KR) ........................ 10-2018-0036786

(51) Int. Cl.
| | |
|---|---|
| *C12N 15/113* | (2010.01) |
| *A61P 3/10* | (2006.01) |
| *C07K 7/06* | (2006.01) |
| *A61K 38/08* | (2019.01) |
| *A61K 31/7088* | (2006.01) |

(52) U.S. Cl.
CPC ...... *C12N 15/1137* (2013.01); *A61K 31/7088* (2013.01); *A61K 38/08* (2013.01); *A61P 3/10* (2018.01); *C07K 7/06* (2013.01); *C12N 2310/122* (2013.01); *C12N 2310/531* (2013.01); *C12N 2320/31* (2013.01)

(58) Field of Classification Search
None
See application file for complete search history.

(56) References Cited

U.S. PATENT DOCUMENTS 7,341,720 B2 * 3/2008 Stefano .................. A61K 38/47
424/94.3

FOREIGN PATENT DOCUMENTS

KR  10-144790 B1  10/2014

OTHER PUBLICATIONS

Kolonin et al. Nature Medicine 2004, vol. 10, pp. 625-632.*
Kahn et al., "Mechanisms linking obesity to insulin resistance and type 2 diabetes", Nature, vol. 444 (2006): 840-846.
Lumeng et al., "Inflammatory links between obesity and metabolic disease", J Clin Invest. 2011; 121(6): 2111-2117.
Serino et al., "Mice Heterozygous for Tumor Necrosis Factor-α Converting Enzyme Are Protected From Obesity-Induced Insulin Resistance and Diabetes", Diabetes, vol. 56, 2007: 2541-2546.
Shoelson et al., "Inflammation and insulin resistance", J Clin Invest. 2006; 116(7): 1793-1801.
Yong et al., "Visceral adipose tissue macrophage-targeted TACE silencing to treat obesity-induced type 2 diabetes", Biomaterials 148 (2017): 81-89.

* cited by examiner

*Primary Examiner* — Tracy Vivlemore
(74) *Attorney, Agent, or Firm* — Adsero IP

(57) ABSTRACT

The present invention relates to a visceral adipose tissue macrophage-targeted non-viral gene/carrier complex for preventing and treating obesity-induced type II diabetes. More specifically, the gene/carrier complex according to the present invention delivers a therapeutic gene in a stable manner in a case of being injected into the body with the visceral adipose tissue macrophages being targeted, and thus exhibits an excellent inhibitory effect against TACE, which allows the gene/carrier complex to be applied for prevention or treatment of obesity-induced type II diabetes.

11 Claims, 10 Drawing Sheets

Specification includes a Sequence Listing.

VISCERAL ADIPOSE TISSUE MACROPHAGE-TARGETED GENE/CARRIER COMPLEX FOR PREVENTING OR TREATING OBESITY-INDUCED TYPE II DIABETES

CROSS-REFERENCE TO RELATED APPLICATION

This application claims priority to and the benefit of Korean Patent Application No. 10-2018-0036786, filed Mar. 29, 2018, the disclosure of which is incorporated herein by reference in its entirety.

SEQUENCE STATEMENT

Incorporated by reference herein in its entirety is the Sequence Listing entitled "G18U10C0823P_US-1_ST25," created Mar. 29, 2018, size of 45 kilobytes.

BACKGROUND

1. Field of the Invention

The present invention relates to a visceral adipose tissue macrophage-targeted non-viral gene/carrier complex for preventing and treating obesity-induced type II diabetes.

2. Discussion of Related Art

Obesity-induced metabolic syndrome is a disease that includes type II diabetes, hyperlipidemia, and the like, and has been emerging as an important problem according to westernization of the current society. Recent studies have suggested that a major cause of this obesity-induced metabolic syndrome is obesity-induced inflammation. Adipose tissue, which is a major tissue of obesity-induced chronic inflammation, contains a large number of immune cells depending on a degree of progression of obesity. Among these, macrophages are biased towards an inflammation form and dominate an inflammatory state of the adipose tissue. Therefore, in visceral adipose tissue with obesity-induced type II diabetes, expression of tumor necrosis factor-α converting enzyme (TACE) is increased, and as a result, excessively increased TACE results in increased concentration of TNF-α inflammatory mediators, so that inflammatory signaling systems are activated to exacerbate obesity-induced inflammation. Therefore, inhibited expression of TACE makes it possible to prevent and treat obesity-induced inflammation. However, a shTACE therapeutic gene itself, which inhibits expression of TACE, exhibits low stability in the human body and has limited application to the human body. Therefore, for successful gene therapy, the therapeutic gene should pass through the plasma membrane and the nuclear membrane, and then be efficiently expressed in the nucleus. For this purpose, it is necessary to enhance stability and delivery effect of the therapeutic gene in the human body by using a gene carrier.

In addition, for the purpose of treating obesity-induced type II diabetes, the therapeutic gene should be delivered to obesity-related visceral adipose tissue targets to decrease side effects caused by off-targeting. In particular, a carrier that targets visceral adipose tissue macrophages which are associated with inflammatory responses in visceral adipose tissue should be used to more selectively inhibit expression of TACE in the visceral adipose tissue macrophages.

SUMMARY OF THE INVENTION

An object of the present invention is to provide a composition for preventing or treating obesity-induced type II diabetes which is used as a complex formed with a gene carrier so as to improve stability and delivery efficiency, in the body, of shRNA which inhibits expression of TACE.

Another object of the present invention is to provide a method for treating obesity-induced type II diabetes, comprising administering a therapeutically effective amount of a gene/carrier complex to a subject in need thereof.

Still another object of the present invention is to provide a peptide which targets visceral adipose tissue macrophages.

In order to achieve the above objects, the present invention provides a composition for preventing or treating obesity-induced type II diabetes, comprising a gene/carrier complex that contains
  (i) at least one shRNA which inhibits expression of tumor necrosis factor-α converting enzyme (TACE) and is selected from the group consisting of SEQ ID NOS: 1 to 5; and
  (ii) a gene carrier which contains the sequences of SEQ ID NO: 6 targeting visceral adipose tissue macrophages and a 9R (SEQ ID NO: 14) peptide.

The present invention also provides a method for treating obesity-induced type II diabetes in a subject in need thereof, comprising administering, to the subject, a therapeutically effective amount of a gene/carrier complex that contains
  (i) at least one shRNA which inhibits expression of tumor necrosis factor-α converting enzyme (TACE) and is selected from the group consisting of SEQ ID NOS: 1 to 5; and
  (ii) a gene carrier which contains the sequences of SEQ ID NO: 6 targeting visceral adipose tissue macrophages and a 9R (SEQ ID NO: 14) peptide.

The present invention also provides a peptide which targets visceral adipose tissue macrophages, comprising the amino acid sequences of SEQ ID NO: 6.

The gene/carrier complex according to the present invention delivers a therapeutic gene in a stable manner in a case of being injected into the body with the visceral adipose tissue macrophages being targeted, and thus exhibits an excellent inhibitory effect against TACE, which allows the gene/carrier complex to be applied for prevention or treatment of obesity-induced type II diabetes.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Figure 1:
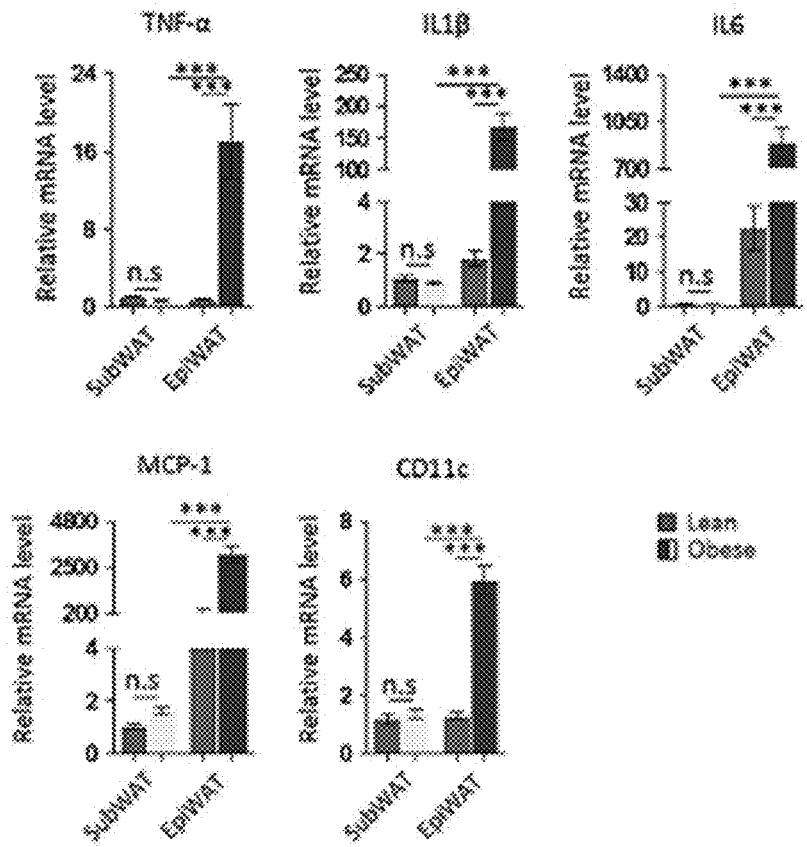
FIG. 1 illustrates results obtained by comparing expression levels of inflammatory mediator (cytokine) genes (TNF-α, IL-1β, IL-6, MCP-1, and CD11c) in adipose tissue due to mice becoming obese.

Hereinafter, the present invention will be described with reference to examples and comparative examples in detail. However, the present invention is not limited to these examples.

The present invention relates to a composition for preventing or treating obesity-induced type II diabetes, comprising a gene/carrier complex that contains
(i) at least one shRNA which inhibits expression of tumor necrosis factor-α converting enzyme (TACE) and is selected from the group consisting of SEQ ID NOS: 1 to 5; and
(ii) a gene carrier which contains the sequences of SEQ ID NO: 6 targeting visceral adipose tissue macrophages and a 9R (SEQ ID NO: 14) peptide.

In addition, the present invention provides a peptide which targets visceral adipose tissue macrophages, comprising the amino acid sequences of SEQ ID NO: 6.

The gene/carrier complex according to the present invention is composed of a complex of shTACE and a gene carrier, in which the gene carrier contains a target sequence targeting visceral adipose tissue macrophages and a 9R peptide.

The shTACE is a shRNA that inhibits expression of human- or mouse-derived TACE, and may be one or more selected from the group consisting of SEQ ID NOS: 1 to 5.

In addition, the shTACE may be in a form of being contained in a plasmid vector and may form a complex with the gene carrier in such a form. Preferably, the plasmid vector containing shTACE may contain at least one base sequences selected from the group consisting of SEQ ID NOS: 7 to 11.

A gene itself exhibits a negative charge due to a phosphoric acid structure. Thus, with only a gene itself, due to electric repulsion, it is not easy to penetrate the plasma membrane exhibiting a negative charge. Therefore, in a case where a gene reacts with a substance exhibiting a positive charge to form a complex, an overall charge of the complex should exhibit a positive charge, so that the complex more easily enters cells and expression of the gene in the cells can be enhanced. Such a substance that increases delivery of a gene into cells is called a gene carrier. The gene carrier means a substance that binds to a gene and helps delivery of the gene for enhanced delivery and increased expression of the gene. Such a gene carrier is mainly a positively charged substance, and forms a gene/carrier complex due to electric interaction between the negatively charged gene and the positively charged gene carrier.

The peptide which targets visceral adipose tissue macrophages may contain the amino acid sequences of SEQ ID NO: 6. It is known that prohibitin is highly expressed in adipose tissue, and it has been found that the above sequences bind to this prohibitin. According to previous studies, it has been found that the above sequences bind to prohibitin of white adipocytes and delivers a gene in an adipocyte-specific manner. In addition, the present invention reveals that the same sequences can target even macrophages in visceral adipocytes, which has significance. Macrophages in visceral adipose tissue play an important role in inflammatory responses of obesity-induced metabolic syndrome. Such macrophages in visceral adipose tissue also express prohibitin. Thus, it can be considered that the same sequences bind to the prohibitin and enter the macrophages (see FIG. 3).

It is possible to use gene carriers known in the art. However, in the present invention, a 9R peptide which is a non-viral gene carrier can be used to overcome low stability of the shTACE. The 9R peptide is composed of 9 arginine sequences.

The shTACE and the gene carrier form a complex due to electric interaction. In order to form a gene-carrier complex (peptoplex) having an excellent therapeutic effect, an optimal ratio between a gene and a gene carrier which form a complex is required. For the ratio, there are various types of ratios such as a weight ratio, a charge ratio, and a nitrogen/phosphorus ratio (N/P ratio). In the present invention, a weight ratio is used.

The gene/carrier complex according to the present invention is preferably formed of the shTACE and the gene carrier at a weight ratio of 1:1.5 to 8 or 1:2 to 4. In a case where the weight ratio is within such a range, the complex can be stably formed, and a size of the complex may be 100 to 200 nm, and more specifically, 120 to 150 nm.

The gene/carrier complex of the present invention can be prepared through a step of mixing the shTACE and a non-viral gene carrier and incubating the mixture.

The incubation is preferably performed at 20° C. to 40° C. for 20 to 40 minutes for the reason that an optimal gene/carrier complex is formed. At a high temperature which exceeds 40° C., interactions between bases in DNA are eliminated, and as a result, DNA is denatured. A carrier is formed due to a polymerization reaction of a peptide. Also, since the carrier is denatured at a high temperature, it is preferable to proceed with complex formation at a temperature of 40° C. or lower. In a case where cells are treated with a complex, it is preferable to proceed with complex formation at a temperature similar to body temperature. On the other hand, in a case where the incubation time exceeds 40 minutes, the gene and the carrier form a precipitate. Thus, it is preferable that the incubation time does not exceed 40 minutes. In addition, after the gene and the carrier are mixed due to electric attraction, it is preferable to incubate the mixture for at least 20 minutes so that a stable state of the resulting complex is maintained.

Short hairpin silencing TACE (shTACE) genes [TACE shRNAs, SEQ ID NOS: 1 to 5] carry a negative charge, and acetate carriers of disulfide bond-polymerized poly(oligoarginine) (PAs-s) carry a positive charge. In a case where these two are mixed and incubated at room temperature for 20 to 40 minutes, a gene/carrier complex can be formed due to electrostatic attraction. After formation of the complex, a final volume is equally adjusted by 3DW, PBS, or the like for each group.

In order to obtain an optimal weight ratio of the gene/carrier complex, a concentration of each of the gene and the gene carrier should first be obtained. Since absorbed ultraviolet radiation is proportional to an amount of DNA, the gene concentration is measured with an ultraviolet spectrophotometer. In order to prevent the gene/carrier complex from precipitating, it is usually preferable to adjust the gene concentration to 1 mg/mL or lower.

The pharmaceutical composition of the present invention may be administered together with a pharmaceutically acceptable carrier. In a case of being orally administered, in addition to the above active ingredient, the pharmaceutical composition may further contain a binder, a lubricant, a disintegrant, an excipient, a solubilizer, a dispersant, a stabilizer, a suspending agent, a colorant, a flavoring agent, and the like. In a case of injections, the pharmaceutical composition of the present invention may be mixed with a buffer, a preserving agent, an analgesic, a solubilizer, an isotonic agent, a stabilizer, and the like, and used. In addition, in a case of being topically administered, the composition of the present invention may use a base, an excipient, a lubricant, a preserving agent, and the like.

Formulations of the composition of the present invention can be prepared in a variety of ways by being mixed with a pharmaceutically acceptable carrier as described above. For example, in a case of being orally administered, the composition may be prepared in the form of tablets, troches, capsules, elixirs, suspensions, syrups, wafers, or the like. In a case of injections, the composition may be prepared in the form of unit dosage ampoules or multiple dosage forms. The composition may be formulated into other forms such as solutions, suspensions, tablets, pills, capsules, and sustained release preparations.

Meanwhile, as examples of suitable carriers, excipients, and diluents for making formulations, lactose, dextrose, sucrose, sorbitol, mannitol, xylitol, erythritol, maltitol, starch, acacia, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oil, or the like may be used. In addition, a filler, an anti-agglomerating agent, a lubricant, a wetting agent, a flavoring agent, a preservative, or the like may be further contained.

The pharmaceutical composition of the present invention can be administered orally or parenterally. For a route of administration of the pharmaceutical composition according to the present invention, the pharmaceutical composition may be administered, for example, but not limited to, via a mouth, aerosol, buccal, skin, intradermal, inhalation, intramuscular, intranasal, intraocular, intrapulmonary, intravenous, intraperitoneal, nose, eye, oral, ear, injection, patch, subcutaneous, sublingual, topical, or transdermal route.

For such clinical administration, the pharmaceutical composition of the present invention can be prepared into a suitable formulation by using a known technique. For example, in a case of being orally administered, the pharmaceutical composition may be mixed with an inert diluent or edible carrier, encapsulated in a hard or soft gelatin capsule, or pressed into tablets, and administered. For oral administration, the active ingredient may be mixed with an excipient and used in the form of ingestible tablets, buccal tablets, troches, capsules, elixirs, suspensions, syrups, wafers, or the like. In addition, various formulations for injection, parenteral administration, and the like can be prepared according to known techniques or commonly used techniques in the art.

An effective dose of the pharmaceutical composition of the present invention varies depending on the patient's body weight, age, sex, health condition, diet, time of administration, method of administration, excretion rate, severity of disease, and the like. The effective dose can be easily determined by an expert of ordinary skill in the art.

A preferred dosage of the pharmaceutical composition of the present invention varies depending on the patient's condition and body weight, severity of disease, drug form, route of administration, and duration, and can be appropriately selected by those skilled in the art. However, the pharmaceutical composition is administered preferably at a daily dose of 0.001 to 100 mg/kg body weight, and more preferably at a daily dose of 0.01 to 30 mg/kg body weight. The administration may be carried out once a day or may be divided into several doses. The gene/carrier complex of the present invention may be present in an amount of 0.0001% to 10% by weight, and preferably 0.001% to 1% by weight, with respect to a total weight of the entire composition.

The pharmaceutical composition of the present invention may be administered, via various routes, to a mammal such as a rat, a mouse, a domesticated animal, and a human. There is no limitation on the method of administration, and the pharmaceutical composition may be administered, for example, orally, rectally, or by intravenous, intramuscular, subcutaneous, intrauterine, or intra-cerebroventricular injection.

The present invention also relates to a method for treating obesity-induced type II diabetes in a subject in need thereof, comprising administering, to the subject, a therapeutically effective amount of a gene/carrier complex that contains
(i) at least one shRNA which inhibits expression of tumor necrosis factor-α converting enzyme (TACE) and is selected from the group consisting of SEQ ID NOS: 1 to 5; and
(ii) a gene carrier which contains the sequences of SEQ ID NO: 6 targeting visceral adipose tissue macrophages and a 9R (SEQ ID NO: 14) peptide.

The subject may be a mammal such as a dog, a cat, a rat, a mouse, and a human, but is not limited thereto.

In the present invention, "treatment" means any action that inhibits, alleviates, or advantageously alters a clinical condition associated with a disease. In addition, the treatment may mean increased survival as compared with a survival rate which is expected in the absence of the treatment. In addition to therapeutic measures, the treatment includes preventive measures at the same time.

As used herein, "effective amount" means an amount necessary to delay or totally stop development or progression of a particular disease to be treated. In the present invention, the gene/carrier complex may be administered in a pharmaceutically effective amount. It will be apparent to those skilled in the art that an appropriate total daily dose may be determined by a practitioner within the scope of sound medical judgment. For purposes of the present invention, it is preferable to differently apply a specific therapeutically effective amount for a particular patient, depending on various factors including type and extent of a response to be achieved, a specific composition, as the case may be, including whether other preparations are used, the patient's age, body weight, general health condition, sex, and diet, time of administration, route of administration, and excretion rate of the composition, duration of treatment, and drugs used together with or simultaneously used with the specific composition, and similar factors well known in the field of medicine.

In the treatment method of the present invention, the gene/carrier complex may be administered by various routes such as orally, rectally, or by intravenous, intramuscular, subcutaneous, intrauterine, or intra-cerebroventricular injection, but not limited thereto.

Hereinafter, the present invention will be described in detail by way of examples. The following examples merely illustrate the present invention, and the scope of the invention is not limited to the following examples. These examples are provided to complete the disclosure of the present invention and to allow those skilled in the art to fully understand the scope of the invention. The present invention is only defined by the scope of the claims.

EXAMPLES

<Example 1> Preparation of Therapeutic Gene/Carrier Complex (Preparation of Therapeutic Gene shTACE)

A plasmid vector which is an RNA interference system and contains a mouse shRNA (shTACE) that inhibits expression of TACE is composed of a total of 6,669 base pairs, and has a U6 promoter. Into the vector was inserted the 19-base sequence ACACCTGCTGCAATAGTGA (SEQ ID NO: 1) so as to construct a vector that selectively inhibits expression of only TACE. SV40 origin and pUC origin were used for proliferation and expression of the vector. An ampicillin-resistant gene was inserted, and puromycin was used as a selection marker to isolate cells with stable expression of shTACE after transfection. The vector was constructed using an eGFP reporter gene such that determination is made on whether the vector is properly inserted. A hairpin loop sequence in the vector is TCAAGAG (which is present in SEQ ID NO: 7). A sequence of the mouse shTACE vector thus prepared is set forth in SEQ ID NO: 7.

On the other hand, therapeutic effects of a gene therapeutic agent system of the present invention were verified through mouse animal experiments.

In order to apply this system clinically, experiments in human cell lines must precede. It is necessary to verify non-toxic and anti-inflammatory effects, and the like of this gene therapeutic agent system in human-derived cells. In this case, a human shTACE gene should be used instead of the mouse shTACE gene. Among several human shTACE vector sequences, a vector sequence that maximally inhibits TACE with the ATS-9R carrier can be an optimal gene therapeutic complex, and four such possible human shTACE vector candidate sequences are set forth in SEQ ID NOS: 8 to 11.

(Preparation of Gene Carrier (ATS-9R) Targeting Visceral Adipose Tissue Macrophages)

A peptide carrier which can target visceral adipose tissue macrophages is composed of ATS peptide sequences (CKGGRAKDC: SEQ ID NO: 6) that can selectively target visceral adipose tissue macrophages, and 9-arginine sequences (RRRRRRRRR, 9R: SEQ ID NO: 14) that facilitates introduction of the carrier into cells. A monomer of the peptide carrier is 'C-KGGRAKD-RRRRRRRRR-C'(SEQ ID NO: 15).

A monomer peptide 'C-KGGRAKD-RRRRRRRRR-C' (SEQ ID NO: 15) was synthesized using a solid-phase fluoreonylmethoxycarbonyl (Fmoc) peptide synthesis method. This is a synthetic method in which each amino acid is extended one by one according to a predetermined sequence order, and an amino acid where amino group is protected with a 9-fluorenylmethoxycarbonyl (Fmoc) group was used. After completion of extension of the peptide chain, treatment with trifluoroacetic acid (TFA) was performed to obtain a peptide in a free form.

(Agarose Gel Electrophoresis)

1 µg of the shTACE therapeutic gene was mixed with various amounts (0.5, 1, 2, 3, and 4 µg) of the ATS-9R carrier and incubated at room temperature for 30 minutes to form gene/carrier complexes. Then, electrophoresis was performed at 100 V for 20 minutes on 0.8% (wt/vol) agarose gel in 0.5×TBE buffer solution, to identify whether a complex is formed.

(Measurement of Surface Charge and Size of Gene/Carrier Complex)

5 µg of the shTACE therapeutic gene was used at various weight ratios (weight ratios of 0.5, 1, 2, 3, and 4) to form shTACE/ATS-9R complexes, and then a total volume thereof was adjusted to 800 µl. Measurement on surface charge and size of the complexes was performed through a Zeta sizer-ZS (Malvern) instrument.

(Analysis for Binding-Ability of ATS Peptide to Primary Adipose Tissue Macrophages)

An obese mouse experimental animal which had consumed high fat for 8 weeks was dissected, and then epididymal adipose tissue (epididymal WAT, a type of visceral adipose tissue) was obtained. Treatment with collagenase at a concentration of 1 mg/mL was performed to obtain a stromal vascular fraction (SVF) in the adipose tissue. For competitive binding-ability analytical experiments, the obtained SVF was first treated with a free-ATS peptide at room temperature for 30 minutes. Then, an ATS peptide (FITC-ATS, 10 µg/mL) to which FITC fluorescence is bound, or a peptide (FITC-NTS, 10 µg/mL) which does not have a targeting ability and to which FITC fluorescence is bound was allowed to react with primary adipose tissue macrophages at room temperature for 30 minutes, and their extent of binding to the macrophages was analyzed by FACS. In addition, a gene/carrier complex (FITC-ATS-9R/shRNA) to which FITC fluorescence is bound was allowed to react with primary adipose tissue macrophages for 4 hours, and the extent that the complex was introduced into the macrophages was analyzed by FACS.

(Cell Culture)

Dulbecco's Modified Eagle Medium (DMEM) and fetal bovine serum (FBS) were purchased from WelGENE (Korea). Mouse-derived macrophage cells RAW 264.7 (mouse macrophages) were purchased from Korean Cell Line Bank and subcultured every other day. The cells were cultured in a complete medium supplemented with 10% FBS, penicillin (100 IU/mL), and streptomycin (100 µm/mL) under a condition at 37° C. and 5% $CO_2$ atmosphere.

(Measurement of TACE mRNA: Isolation of RNA and Real-Time PCR)

$4 \times 10^4$ mouse-derived macrophage cells (RAW 264.7) per well of a cell culture plate were cultured for 24 hours. The macrophage cells were treated with the shTACE/ATS-9R gene/carrier complex for 24 hours. Then, the cells were homogenized using the RNeasy Lipid Tissue Mini Kit (Qiagen), and only RNA was isolated. The isolated RNA was reacted with reverse transcriptase to synthesize each complementary cDNA for 1 µg of RNA for each group. Then, a relative amount of TACE mRNA for an intrinsic gene GAPDH which is a control was measured by real-time PCR using the Cyber premix Ex Taq RT-PCR kit (forward and reverse primers for TACE were 5'-GTACGTC-GATGCAGAGCAAA-3' (SEQ ID NO: 12) and 5'-AAACCAGAACAGACCCAACG-3' (SEQ ID NO: 13), respectively).

(ELISA Measurement of Water-Soluble (Inflammatory) TNF-α)

$4 \times 10^4$ mouse-derived macrophage cells (RAW 264.7) per well of a cell culture plate were cultured for 24 hours. Then, treatment with 100 ng/mL of lipopolysaccharide (LPS) per well was performed, so that the macrophage cells were activated to induce an inflammatory state. The activated macrophages, that is, the macrophages in an inflammatory state were treated with the shTACE/ATS-9R gene/carrier complex for 48 hours. Then, a cell medium was obtained from each well, and subjected to centrifugation at 13,000 rpm at 4° C. Supernatant of the medium was used as a sample. An amount of water-soluble TNF-α inflammatory mediators (cytokines) from the medium sample was measured by sandwich ELISA.

(Injection of Gene/Carrier Complex)

After completion of modeling of experimental animals with obesity and obesity-induced type II diabetes, a gene/carrier complex (shTACE/ATS-9R complex) formed of 15 µg of the shTACE therapeutic gene and 45 µg of the ATS-9R carrier which are at an optimal weight ratio of 1:3 was intraperitoneally injected thereinto twice a week for a total of 4 weeks. An amount of the gene/carrier complex used to treat the experimental animals was about 0.3 mg/kg.

(Identification of Biodistribution)

A gene/carrier complex (Cy5.5-ATS-9R/shRNA) to which Cy5.5 fluorescence is bound was intraperitoneally injected into obese mouse experimental animals which had consumed high fat for 8 weeks. Twelve or twenty-four hours after injection of the gene/carrier complex, the mouse experimental animal was dissected to obtain epididymal adipose tissue (epididymal WAT, a type of visceral adipose tissue), subcutaneous fat, liver, spleen, heart, lung, and kidney. The whole fluorescent image of the tissue was measured with the Image Station (Kodak). In addition, the tissue was homogeneously ground and a relative fluorescence value in the tissue was also quantitatively measured. In addition, a gene/carrier complex (FITC-ATS-9R/shRNA) to which FITC fluorescence is bound was intraperitoneally injected into obese mouse experimental animals which had consumed high fat for 8 weeks. 4 hours after injection of the gene/carrier complex, macrophage cells and non-macrophage cells in the adipose tissue, the liver, and the spleen were distinguished (using an anti-F4/80 antibody), and then the extent that the gene/carrier complex is introduced in each cell was analyzed by FACS.

(Insulin Tolerance Test (ITT) and Glucose Tolerance Test (GTT)).

For the mouse experimental animals, initial blood glucose values were measured using an Accu-Chek Active model GC kit after 6 hours (at the time of conducting ITT) or 16 hours (at the time of conducting GTT) of fasting. Then, intraperitoneal injection of insulin (0.75 U/kg, at the time of conducting ITT) or glucose (3 g/kg, at the time of conducting GTT) was immediately carried out. Then, blood glucose was measured at time intervals of 15 minutes, 30 minutes, 60 minutes, 90 minutes, and 120 minutes.

(Ex Vivo Sampling)

After completion of treatment with the gene/carrier complex, the mouse experimental animals with obesity-induced type II diabetes were dissected to obtain epididymal adipose tissue (epididymal WAT, a type of visceral adipose tissue) and subcutaneous fat. The adipose tissue sample was physically crushed and then treated with collagenase at a concentration of 1 mg/mL. The resultant was centrifuged at 400 g for 10 minutes to obtain SVF. An expression level of TACE proteins in the obtained SVF sample was measured by Western blotting. In addition, the obtained SVF sample was homogenously broken to obtain RNA. Expression levels of TACE, TNF-α, IL-6, IL-1β, MCP-1, CD11b, CD11c, prohibitin, and the like were quantitatively measured at an mRNA level. Finally, blood TNF-α, IL-6, IL-1β, and MCP-1 inflammatory mediators were quantitatively measured by ELISA.

<Example 2> Identification of Overexpression of Major Inflammatory Cytokine Genes in Obese Visceral Adipose Tissue According to previous studies on obesity, it has been found that visceral fat inflammation in human obesity and animal obesity is closely related to type II diabetes and obesity-induced metabolic disease. Based on these studies, in order to identify visceral adipose tissue-preferential overexpression of inflammatory cytokine genes, mRNA levels of subcutaneous adipose tissue and visceral adipose tissue inflammatory cytokine genes were identified by RT-PCR in rats for which obesity had been induced with high fat diet and rats for which obesity had not been induced.

Figure 2:
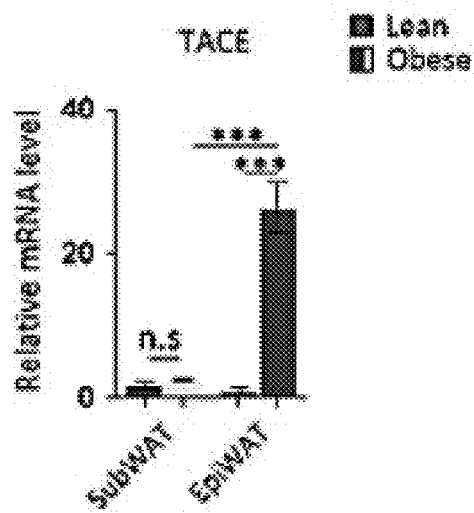
FIG. 2 illustrates results obtained by comparing expression levels of the TACE gene in adipose tissue due to mice becoming obese.

It was identified that inflammatory cytokine genes including TNF-α and IL-1β are overexpressed in visceral adipose tissue relative to subcutaneous adipose tissue (FIG. 1). In a case where an mRNA level of TACE in obese visceral adipose tissue is measured prior to application of the shTACE therapeutic gene complex of the present invention, it was identified that TACE is overexpressed in a visceral adipose tissue-preferential manner similarly to expression of other inflammatory cytokines, so that suitability thereof as a therapeutic target gene was verified (FIG. 2).

Figure 3:
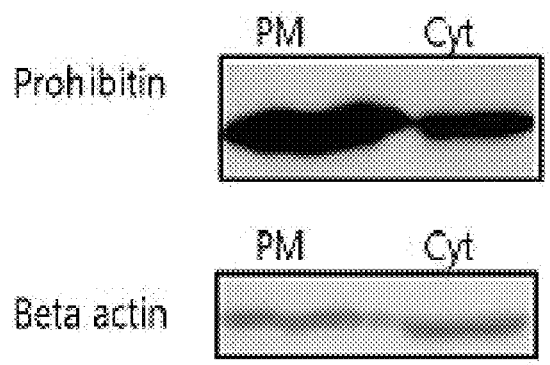
FIG. 3 illustrates results obtained by separating the plasma membrane and the cytosol from mouse-derived macrophage cells (Raw 264.7 cell line) and then qualitatively measuring a degree of expression of prohibitin proteins by Western blotting.

In addition, it was identified that prohibitin is expressed in mouse-derived macrophage cells (Raw 264.7 cell line). The plasma membrane and the cytosol were separated from the macrophage cells, and expression of prohibitin was checked. It was identified that prohibitin is expressed in both the plasma membrane and the cytosol. This is a result which supports that this ATS sequence, which is known to be capable of binding to prohibitin, is capable of binding to macrophages (FIG. 3).

Figure 4:
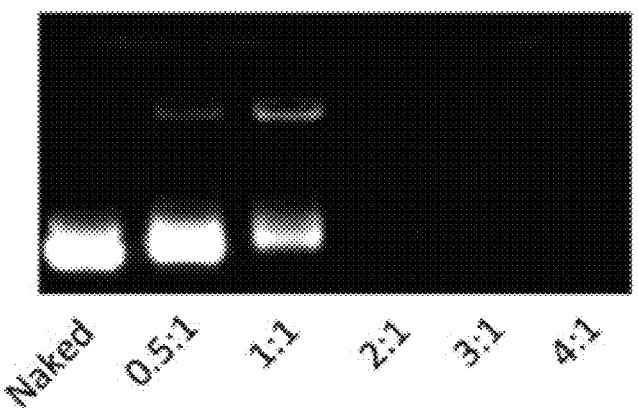
FIG. 4 illustrates results obtained by electrophoretically identifying formation of a complex according to weight ratios of a shTACE/ATS-9R gene/carrier complex [Naked means no treatment with ATS-9R carrier, 0.5:1 means ATS-9R:shTACE=0.5:1, 1:1 means ATS-9R:shTACE=1:1, 2:1 means ATS-9R:shTACE=2:1, 3:1 means ATS-9R:shTACE=3:1, and 4:1 means ATS-9R:shTACE=4:1].
Figure 5:
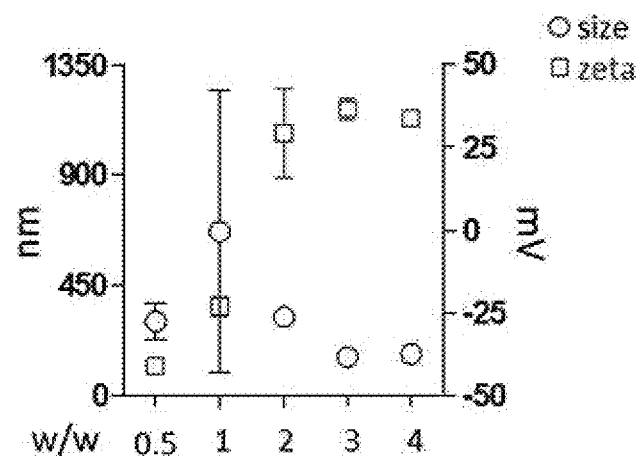
FIG. 5 illustrates results which show zeta potential and nanoparticle size according to weight ratios of the shTACE/ATS-9R gene/carrier complex. [w/w 0.5 means ATS-9R:shTACE=0.5:1, w/w 1 means ATS-9R:shTACE=1:1, w/w 2 means ATS-9R:shTACE=2:1, w/w 3 means ATS-9R:shTACE=3:1, and w/w 4 means ATS-9R:shTACE=4:1].

<Example 3> Optimization of shTACE/ATS-9R Gene/Carrier Complex and Verification of its Ability to Target Adipose Tissue Macrophages For formation and optimization of a complex between the gene carrier ATS-9R and the shTACE therapeutic gene, in a case where electrophoresis results (FIG. 4), and particle size and surface charge (FIG. 5) are checked, it was identified that the gene carrier stably forms a complex with the gene at a weight ratio of 1:3 or more, and a complex size of 150 nm is formed.

Figure 6:
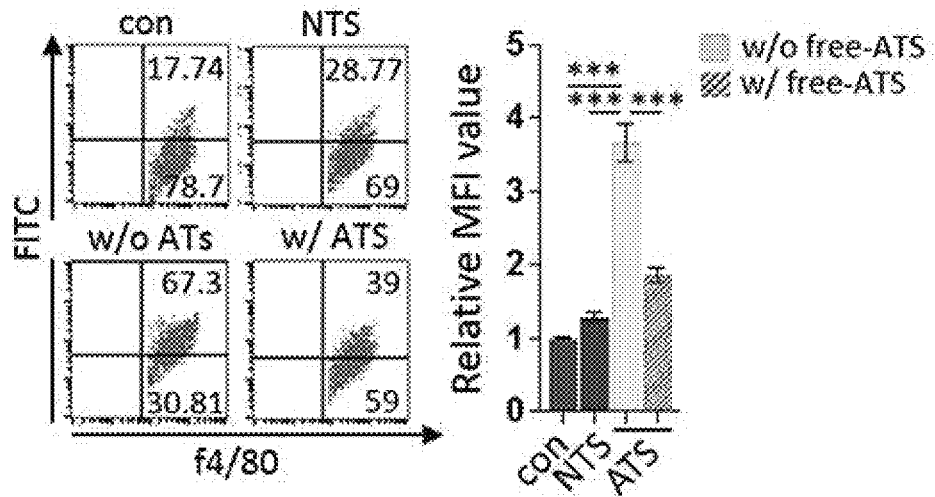
FIG. 6 illustrates results of verifying a binding ability of a conventional ATS peptide to surfaces of mouse adipose tissue macrophages.

In a case where an ATS peptide labeled with fluorescence (FITC) was used to check adherence thereof to adipose tissue macrophage cells (F4/80+ cells), the peptide exhibited a high binding ability relative to a non-targeting sequence (NTS). In a case where treatment was performed together with a free-ATS not labeled with fluorescence, decreased fluorescence was exhibited, so that target receptor-specific cell adhesion of the peptide was verified (FIG. 6).

Figure 7:
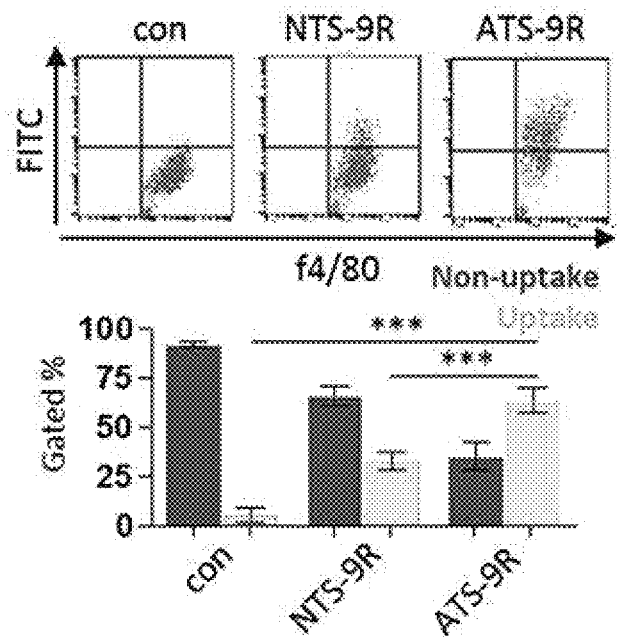
FIG. 7 illustrates results of verifying, with flow cytometry, entry of the shTACE/ATS-9R gene/carrier complex into mouse adipose tissue macrophages.

Based on such an ability to target the primary adipose tissue macrophages, in a case of checking an ability of the shTACE/ATS-9R gene/carrier complex to enter adipose tissue F4/80+ macrophage cells, it was identified that the shTACE/ATS-9R gene/carrier complex exhibits 70% or more entry into the cells relative to a shTACE/NTS-9R complex (FIG. 7).

Figure 8:
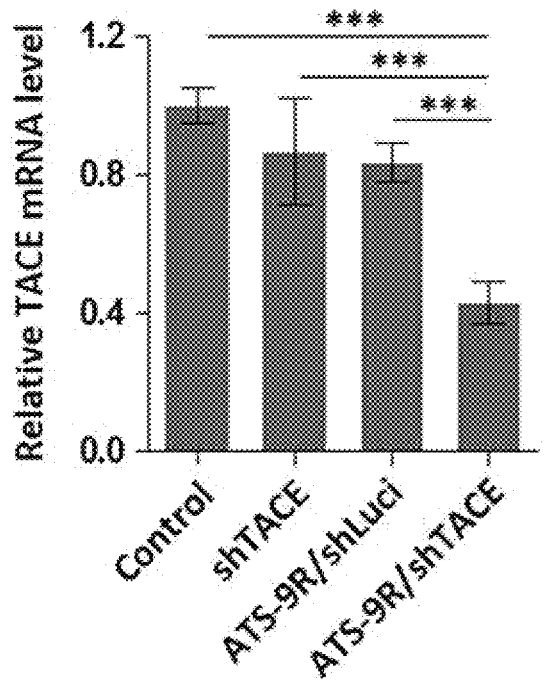
FIG. 8 illustrates results of verifying an ability of the shTACE/ATS-9R gene/carrier complex to deliver the shTACE gene to mouse-derived macrophage cells by measuring a degree of expression of TACE at an mRNA level.

<Example 4> Verification of Anti-Inflammatory Effect of shTACE/ATS-9R Gene/Carrier Complex In order to identify inhibition of TACE gene by the shTACE/ATS-9R gene/carrier complex and an anti-inflammatory effect caused thereby, mouse-derived macrophage cells (Raw264.7) were treated with the shTACE/ATS-9R gene/carrier complex, and mRNA of the TACE gene was quantified by RT-PCR. As a result, it was identified that the TACE gene is decreased (FIG. 8).

Figure 9:
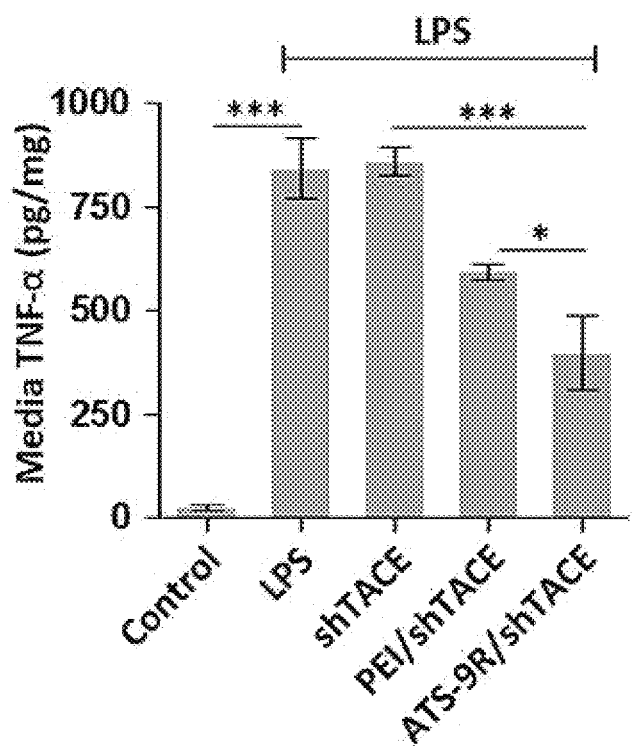
FIG. 9 illustrates results of verifying an anti-inflammatory effect of the shTACE/ATS-9R gene/carrier complex due to delivery of the shTACE gene to mouse-derived macrophage cells by measuring a level of TNF-α.

In order to identify whether such inhibition of the TACE gene by the shTACE/ATS-9R gene/carrier complex inhibits an actual inflammatory response, an inflammatory response in mouse-derived macrophage cells caused by lipopolysaccharide (LPS) was quantified by TNF-α ELISA. It was identified that a TACE-inhibited group exhibits a 50% decrease relative to an untreated group (FIG. 9).

Figure 10:
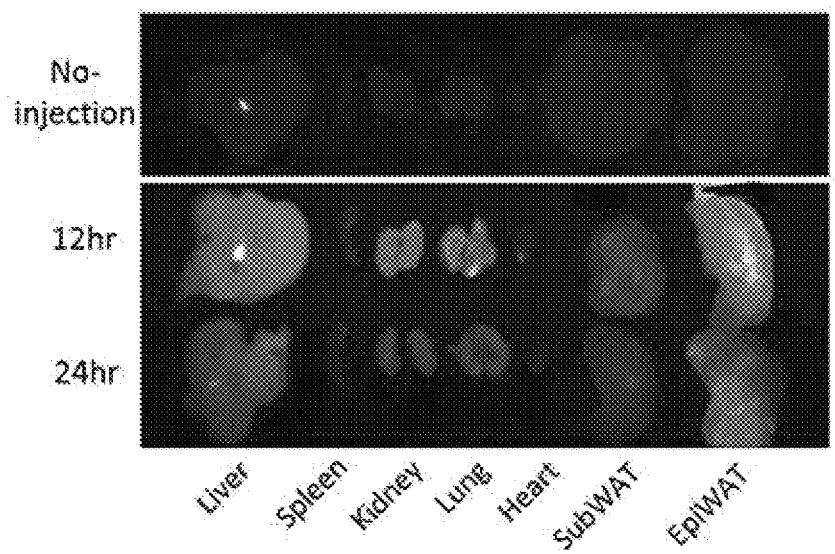
FIG. 10 illustrates results obtained by measuring, with fluorescence imaging, a degree of a fluorescence-labeled shTACE/ATS-9R gene/carrier complex being distributed in mouse organs [liver, spleen, kidney, lung, heart, subcutaneous white adipose tissue (SubWAT), and epididymal white adipose tissue (EpiWAT)].
Figure 11:
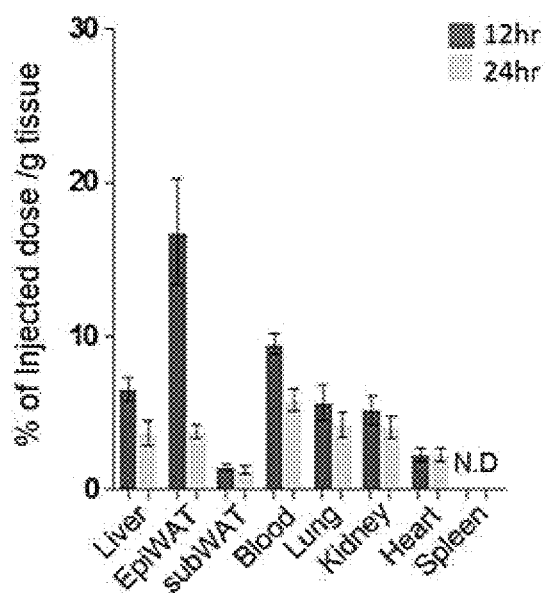
FIG. 11 illustrates results obtained by quantifying a degree of the fluorescence-labeled shTACE/ATS-9R gene/carrier complex being distributed in mouse organs [liver, spleen, kidney, lung, heart, subcutaneous white adipose tissue (SubWAT), epididymal white adipose tissue (EpiWAT), and blood].

<Example 5> Verification of Ability of shTACE/ATS-9R Gene/Carrier Complex to Target Visceral Adipose Tissue Macrophages In order to verify an ability of the shTACE/ATS-9R gene/carrier complex to deliver a gene in a visceral adipose tissue-specific manner, intraperitoneal administration of a gene (30 μg)/carrier (90 μg) complex labeled with fluorescence (Cy5.5) was carried out. 12 hours and 24 hours later, major organs, visceral adipose tissue, and subcutaneous adipose tissue were extracted and the Cy5.5 fluorescence was imaged (FIG. 10). In a case of being quantified, it was identified that the fluorescence is highly accumulated in the visceral adipose tissue (FIG. 11).

Figure 12:
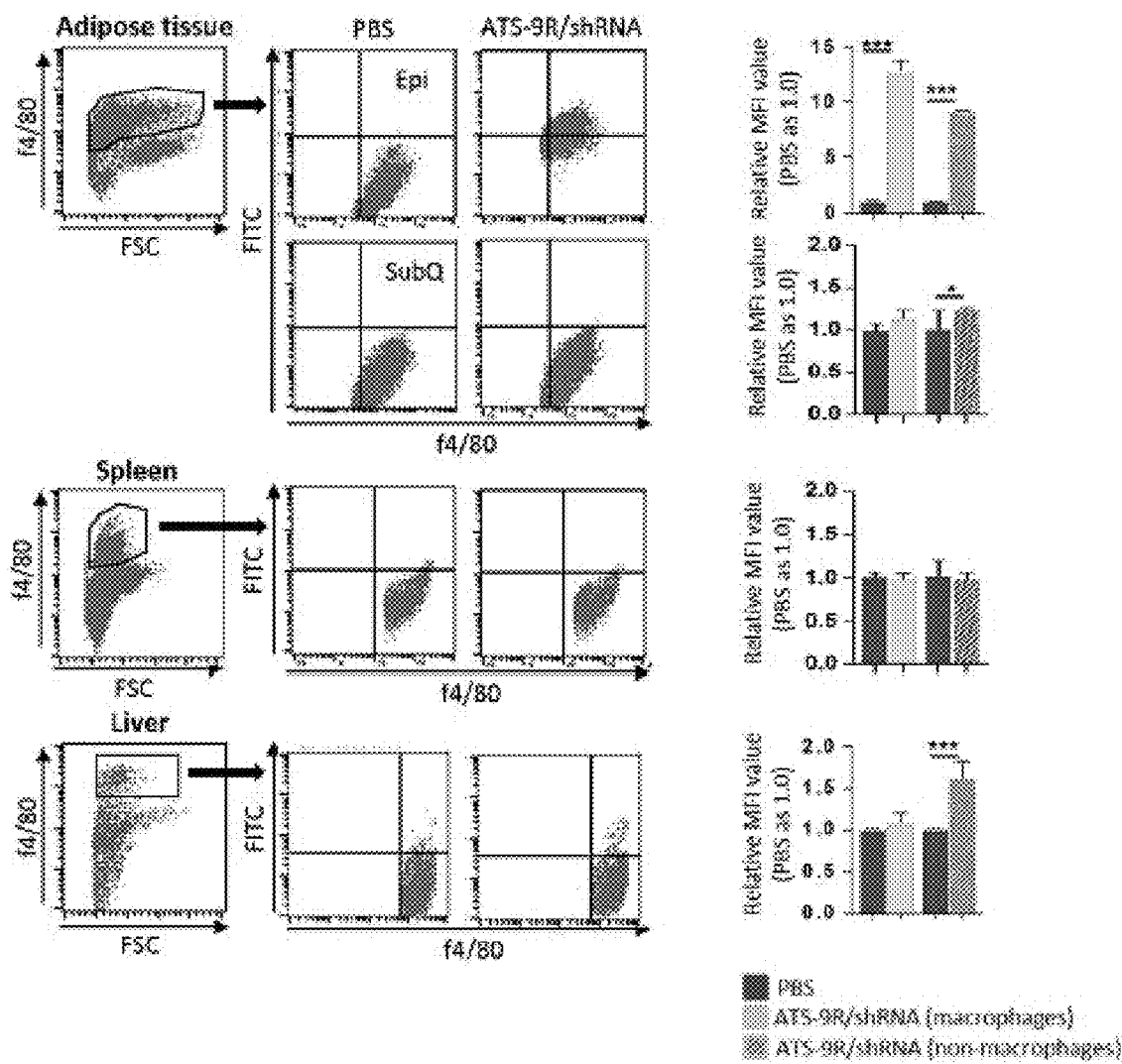
FIG. 12 illustrates results of quantifying, with flow cytometry, entry of the fluorescence-labeled shTACE/ATS-9R gene/carrier complex into mouse organ macrophages.

In order to verify an ability of the shTACE/ATS-9R gene/carrier complex to target macrophages in adipose tissue, intraperitoneal administration of the shTACE/ATS-9R gene/carrier complex was carried out. 3 to 4 hours after intraperitoneal administration, entry thereof into the adipose tissue macrophages was identified by flow cytometry (FIG. 12).

<Example 6> Anti-Inflammatory Effect of shTACE/ATS-9R Gene/Carrier Complex, and Ameliorating Effect Caused Thereby on Type II Diabetes In type II diabetes, insulin receptor sensitivity in the body is decreased due to obesity-induced chronic inflammation, so that a response to insulin is decreased and blood glucose is consistently maintained at a high level. In order to verify a therapeutic effect of the shTACE/ATS-9R gene/carrier complex on obesity inflammation and type II diabetes, a gene (0.35 mg/kg dose)/carrier complex was intraperitoneally administered 8 times for 4 weeks. One week after the last administration, insulin tolerance and glucose tolerance were tested.

Figure 13:
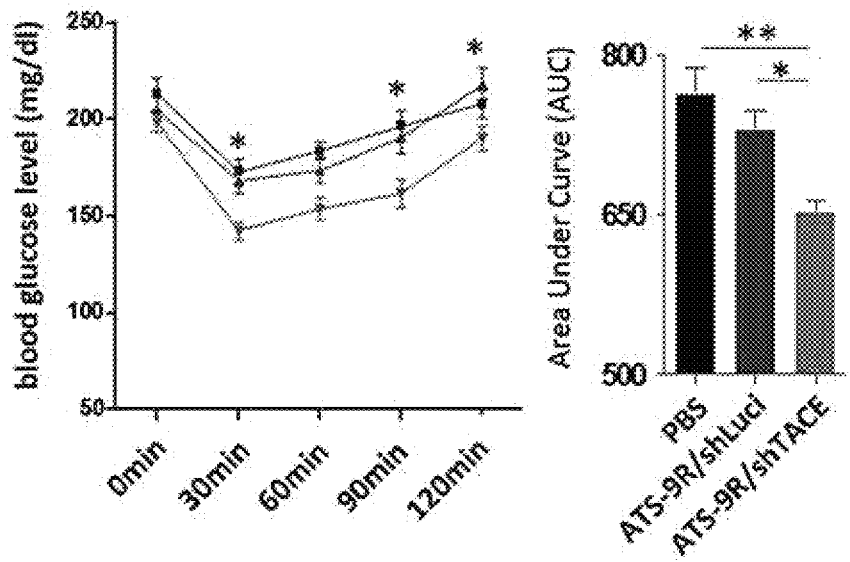
FIG. 13 illustrates results obtained by identifying, via blood glucose quantification, improved insulin tolerance due to an anti-inflammatory effect of the shTACE/ATS-9R gene/carrier complex.
Figure 14:
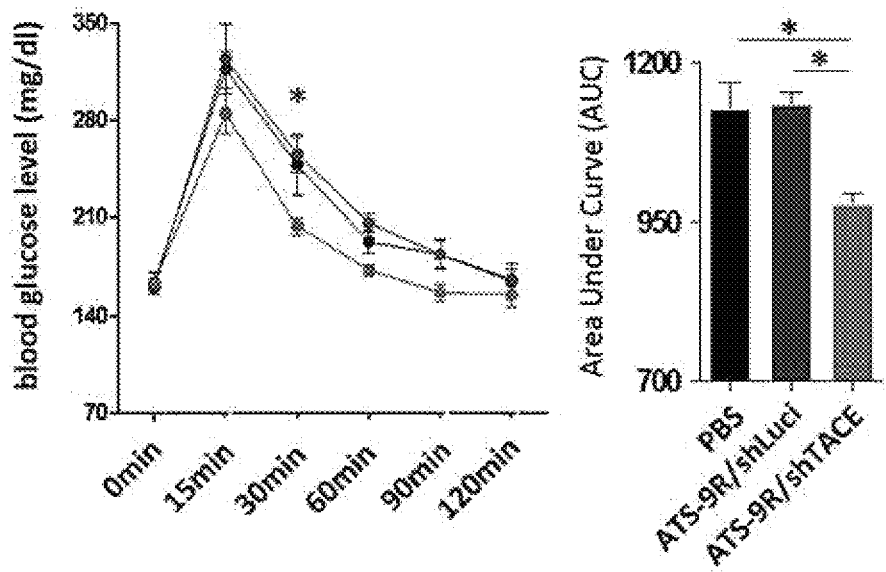
FIG. 14 illustrates results obtained by identifying, via blood glucose quantification, improved glucose tolerance due to an anti-inflammatory effect of the shTACE/ATS-9R gene/carrier complex.

It was possible to identify that high insulin responsiveness is exhibited in the shTACE gene/carrier complex-administered group relative to the PBS-administered group and the negative control gene/carrier complex-administered group (FIG. 13). Responsiveness to glucose administration was also enhanced (FIG. 14).

Figure 15:
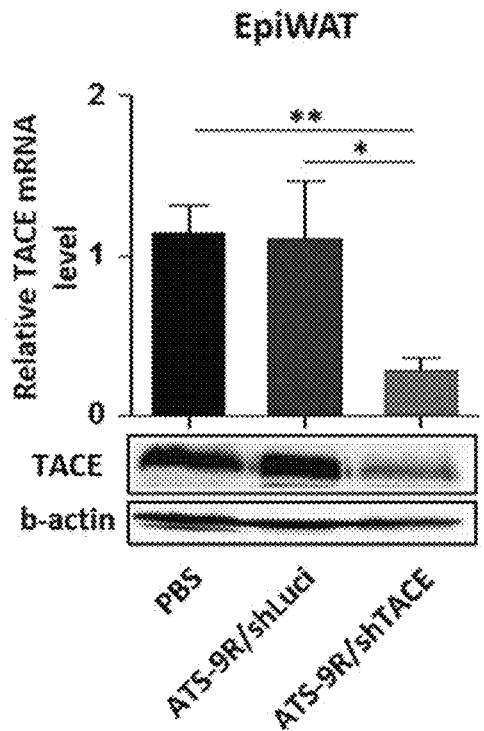
FIG. 15 illustrates results obtained by identifying an inhibitory effect against mRNA of the TACE gene and against expression of TACE in visceral adipose tissue macrophages, following treatment with the shTACE/ATS-9R gene/carrier complex.
Figure 18:
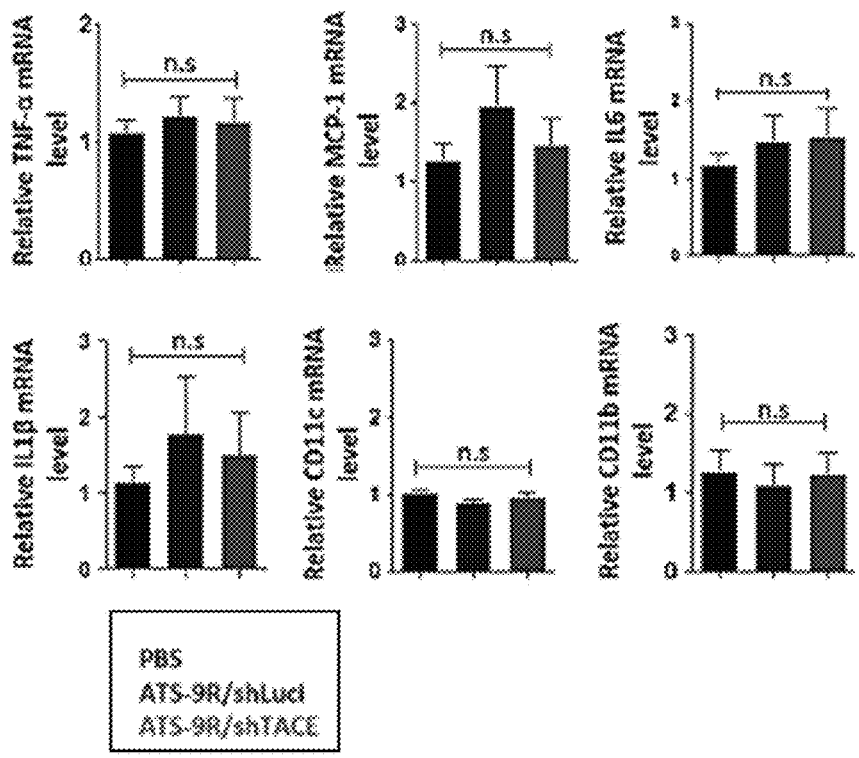
FIG. 18 illustrates results obtained by identifying an inhibitory effect against mRNAs of subcutaneous adipose tissue inflammatory mediator (cytokine) genes (TNF-α, IL-β, IL-6, MCP-1, and CD11c), following treatment with the shTACE/ATS-9R gene/carrier complex.

In order to verify that such improved insulin tolerance is due to an anti-inflammatory effect caused by delivery of the therapeutic gene, adipose tissue of a mouse was extracted to measure an expression level of mRNAs of inflammatory cytokine genes including TACE. It was possible to identify that the TACE gene (FIG. 15), and TNF-α and inflammatory cytokine genes (FIG. 18) exhibit decreased mRNA expression in visceral adipose tissue.

Figure 16:
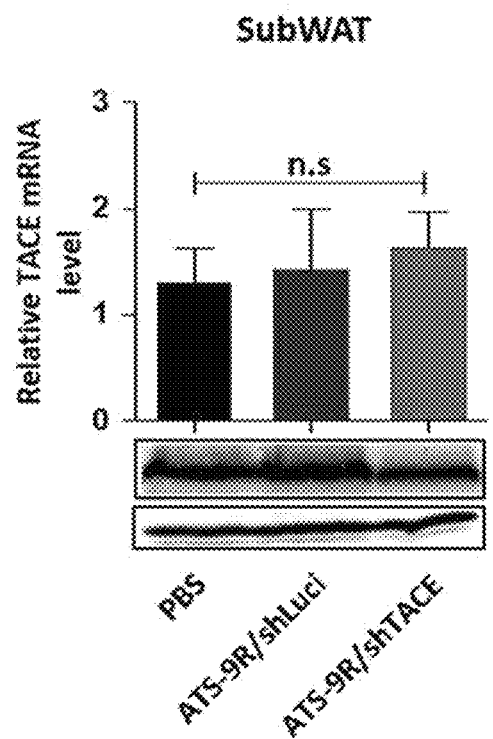
FIG. 16 illustrates results obtained by identifying an inhibitory effect against mRNA of the TACE gene and against expression of TACE in subcutaneous adipose tissue macrophages, following treatment with the shTACE/ATS-9R gene/carrier complex.
Figure 17:
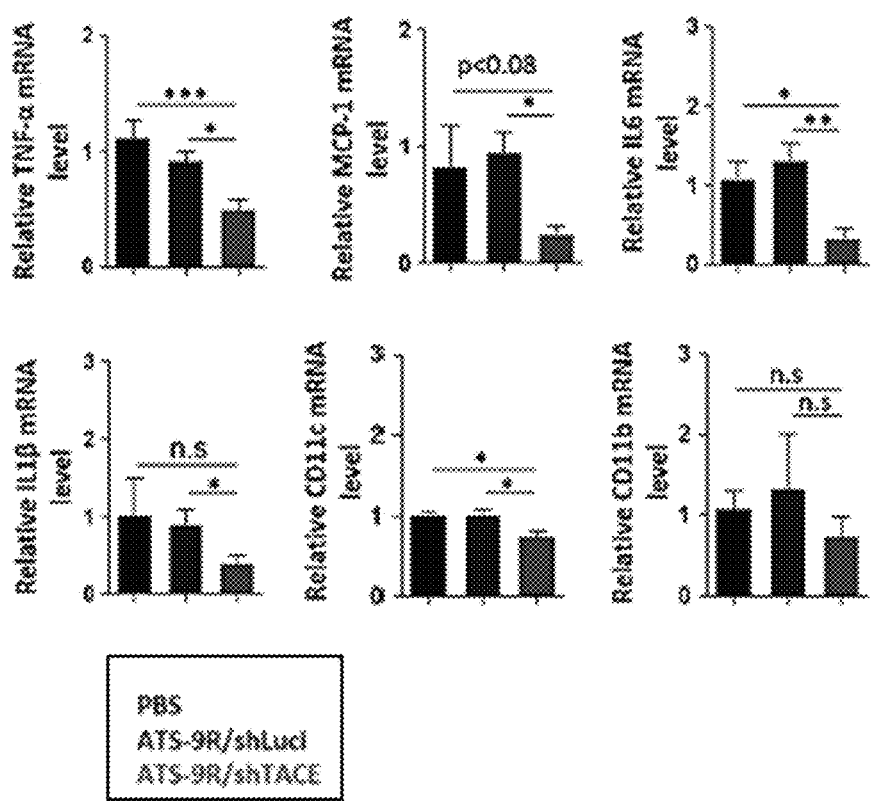
FIG. 17 illustrates results obtained by identifying an inhibitory effect against mRNAs of visceral adipose tissue inflammatory mediator (cytokine) genes (TNF-α, IL-1β, IL-6, MCP-1, and CD11c), following treatment with the shTACE/ATS-9R gene/carrier complex.

In addition, it was identified that expression of the TACE gene and the anti-inflammatory cytokine genes is not greatly inhibited in subcutaneous adipose tissues relative to visceral adipose tissue (FIG. 16), and it was identified that a therapeutic effect caused by delivery of the therapeutic gene arises from inhibition of visceral fat inflammation (FIG. 17).

Figure 19:
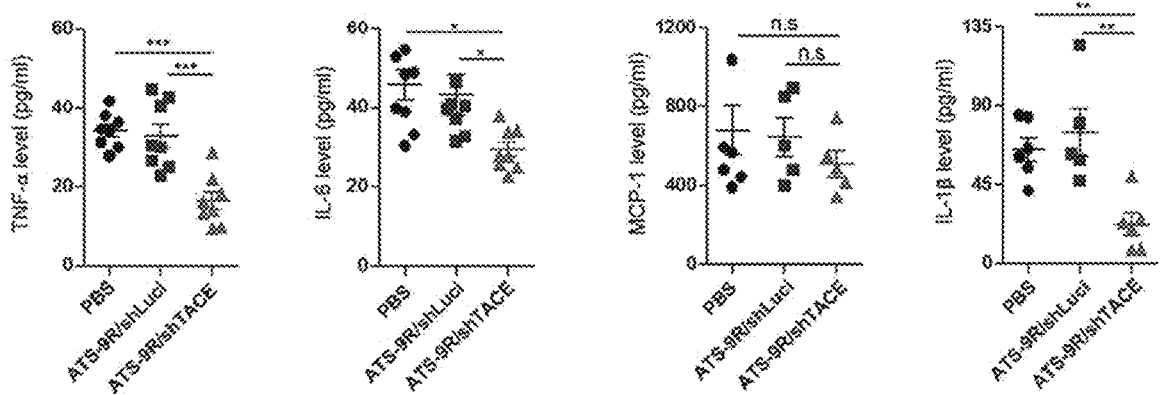
FIG. 19 illustrates results obtained by identifying, via blood inflammatory mediator (cytokine) quantification, an systemic inflammation inhibitory effect caused by an adipose tissue anti-inflammatory effect, following treatment with the shTACE/ATS-9R gene/carrier complex.

<Example 7> Verification of Systemic Inflammation Inhibitory Effect of shTACE/ATS-9R Gene/Carrier Complex Type II diabetes and metabolic disease caused by obesity result from systemic chronic inflammation caused by adipose tissue inflammation. Therefore, in order to identify that inhibition of adipose tissue inflammation by the shTACE/ATS-9R gene/carrier complex ameliorates type II diabetes through inhibition of systemic inflammation, blood inflammatory cytokines were quantified by ELISA. It was identified that four inflammatory cytokines including TNF-α and IL-β are decreased in the shTACE/ATS-9R gene/carrier complex-administered group (FIG. 19).

What is claimed is:

1. A composition for preventing or treating obesity-induced type II diabetes, comprising:
    a gene/carrier complex that contains
    (i) at least one shRNA which inhibits expression of tumor necrosis factor-α converting enzyme (TACE) and is selected from the group consisting of SEQ ID NOS: 1 to 5; and
    (ii) a gene carrier which contains the sequences of SEQ ID NO: 6 targeting visceral adipose tissue macrophages and a 9R (SEQ ID NO: 14) peptide.

2. The composition according to claim 1, wherein the shRNA is in a form of being contained in a plasmid vector.

3. The composition according to claim 2, wherein the plasmid vector containing the shRNA contains at least one base sequences selected from the group consisting of SEQ ID NOS: 7 to 11.

4. The composition according to claim 1, wherein the shRNA which inhibits expression of TACE and the gene carrier are contained at a weight ratio of 1:1.5 to 8.

5. The composition according to claim 1, wherein the gene/carrier complex is formed through electrostatic attraction between the shRNA and the gene carrier.

6. A method for treating obesity-induced type II diabetes in a subject in need thereof, comprising:
    administering, to the subject, a therapeutically effective amount of a gene/carrier complex that contains
    (i) at least one shRNA which inhibits expression of tumor necrosis factor-α converting enzyme (TACE) and is selected from the group consisting of SEQ ID NOS: 1 to 5; and
    (ii) a gene carrier which contains the sequences of SEQ ID NO: 6 targeting visceral adipose tissue macrophages and a 9R (SEQ ID NO: 14) peptide.

7. The method according to claim 6, wherein the shRNA is in a form of being contained in a plasmid vector.

8. The method of claim 7, wherein the plasmid vector containing the shRNA contains at least one base sequences selected from the group consisting of SEQ ID NOS: 7 to 11.

9. The method according to claim 6, wherein the shRNA for inhibiting expression of TACE and the gene carrier are contained at a weight ratio of 1:1.5 to 8.

10. The method according to claim 6, wherein the gene/carrier complex is formed through electrostatic attraction between the shRNA and the gene carrier.

11. The method according to claim 6, wherein the gene/carrier complex is administered via a mouth, aerosol, buccal, skin, intradermal, inhalation, intramuscular, intranasal, intraocular, intrapulmonary, intravenous, intraperitoneal, nose, eye, oral, ear, injection, patch, subcutaneous, sublingual, topical, or transdermal route.

* * * * *

SEQUENCE LISTING

```
<160> NUMBER OF SEQ ID NOS: 15

<210> SEQ ID NO 1
<211> LENGTH: 19
<212> TYPE: DNA
<213> ORGANISM: Artificial Sequence
<220> FEATURE:
<223> OTHER INFORMATION: mouse shTACE

<400> SEQUENCE: 1
acacctgctg caatagtga                                              19

<210> SEQ ID NO 2
<211> LENGTH: 21
<212> TYPE: DNA
<213> ORGANISM: Artificial Sequence
<220> FEATURE:
<223> OTHER INFORMATION: human shTACE #1

<400> SEQUENCE: 2
ggagatttgt taatgatacc a                                           21

<210> SEQ ID NO 3
<211> LENGTH: 21
<212> TYPE: DNA
<213> ORGANISM: Artificial Sequence
<220> FEATURE:
<223> OTHER INFORMATION: human shTACE #2

<400> SEQUENCE: 3
cctggttaca actcatgaat t                                           21

<210> SEQ ID NO 4
<211> LENGTH: 21
<212> TYPE: DNA
<213> ORGANISM: Artificial Sequence
<220> FEATURE:
<223> OTHER INFORMATION: human shTACE #3

<400> SEQUENCE: 4
ggcgattaat gctacttgca a                                           21

<210> SEQ ID NO 5
<211> LENGTH: 21
<212> TYPE: DNA
<213> ORGANISM: Artificial Sequence
<220> FEATURE:
<223> OTHER INFORMATION: human shTACE #4

<400> SEQUENCE: 5
ccattgtgtg gataagaaat t                                           21

<210> SEQ ID NO 6
<211> LENGTH: 9
<212> TYPE: PRT
<213> ORGANISM: Artificial Sequence
<220> FEATURE:
<223> OTHER INFORMATION: Adipose tissue Targeting Sequence

<400> SEQUENCE: 6

Cys Lys Gly Gly Arg Ala Lys Asp Cys
```

-continued

<210> SEQ ID NO 7
<211> LENGTH: 6669
<212> TYPE: DNA
<213> ORGANISM: Artificial Sequence
<220> FEATURE:
<223> OTHER INFORMATION: mouse shTACE vector

<400> SEQUENCE: 7

```
gaattcgcgg cccctagcttg ggatctttgt gaaggaacct tacttctgtg gtgtgacata        60
attggacaaa ctacctacag agatttaaag ctctaaggta aatataaaat ttttaagtgt       120
ataatgtgtt aaactagctg catatgcttg ctgcttgaga gttttgctta ctgagtatga       180
tttatgaaaa tattatacac aggagctagt gattctaatt gtttgtgtat tttagattca       240
cagtcccaag gctcatttca ggcccctcag tcctcacagt ctgttcatga tcataatcag       300
ccataccaca tttgtagagg ttttacttgc tttaaaaaac ctcccacacc tcccctgaa        360
cctgaaacat aaaatgaatg caattgttgt tgttaacttg tttattgcag cttataatgg       420
ttacaaataa agcaatagca tcacaaattt cacaaataaa gcattttttt cactgcattc       480
tagttgtggt ttgtccaaac tcatcaatgt atcttatcat gtctggatcg atcctgcatt       540
aatgaatcgg ccaacgcgcg gggagaggcg gtttgcgtat tggctggcgt aatagcgaag       600
aggcccgcac cgatcgccct tcccaacagt tgcgcagcct gaatggcgaa tgggacgcgc       660
cctgtagcgg cgcattaagc gcggcgggtg tggtggttac gcgcagcgtg accgctacac       720
ttgccagcgc cctagcgccc gctcctttcg ctttcttccc ttcctttctc gccacgttcg       780
ccggctttcc ccgtcaagct ctaaatcggg gctccctttg ggttccga tttagtgctt        840
tacggcacct cgaccccaaa aaacttgatt agggtgatgg ttcacgtagt gggccatcgc       900
cctgatagac ggttttcgc cctttgacgt tggagtccac gttctttaat agtggactct        960
tgttccaaac tggaacaaca ctcaacccta tctcggtcta ttcttttgat ttataaggga      1020
ttttgccgat ttcggcctat tggttaaaaa atgagctgat ttaacaaata tttaacgcga      1080
attttaacaa aatattaacg tttacaattt cgcctgatgc ggtattttct ccttacgcat      1140
ctgtgcggta tttcacaccg catacgcgga tctgcgcagc accatggcct gaaataacct      1200
ctgaaagagg aacttggtta ggaaccttct gaggcgaaa gaaccagctg tggaatgtgt       1260
gtcagttagg gtgtggaaag tccccaggct ccccagcagg cagaagtatg caaagcatgc      1320
atctcaatta gtcagcaacc aggtgtggaa agtcccagg ctccccagca ggcagaagta       1380
tgcaaagcat gcatctcaat tagtcagcaa ccatagtccc gcccctaact ccgcccatcc      1440
cgcccctaac tccgcccagt tccgcccatt ctccgcccca tggctgacta atttttttta      1500
tttatgcaga ggccgaggcc gcctcggcct ctgagctatt ccagaagtag tgaggaggct      1560
tttttggagg cctaggcttt tgcaaaaagc ttgattcttc tgacacaaca gtctcgaact      1620
taaggctaga gccaccatga ccgagtacaa gcccacggtg cgcctcgcca cccgcgacga      1680
cgtccccagg gccgtacgca ccctcgccgc cgcgttcgcc gactacccg ccacgcgcca       1740
caccgtcgat ccggaccgcc acatcgagcg ggtcaccgag ctgcaagaac tcttcctcac      1800
gcgcgtcggg ctcgacatcg gcaaggtgtg gtcgcggac gacggcgccg cggtggcggt       1860
ctggaccacg ccggagagcg tcgaagcggg ggcggtgttc gccgagatcg gcccgcgcat      1920
ggccgagttg agcggttccc ggctggccgc gcagcaacag atggaaggcc tcctggcgcc      1980
gcaccggccc aaggagcccg cgtggttcct ggccaccgtc ggcgtctcgc ccgaccacca      2040
```

```
gggcaagggt ctgggcagcg ccgtcgtgct ccccggagtg gaggcggccg agcgcgccgg    2100
ggtgcccgcc ttcctggaga cctccgcgcc ccgcaacctc cccttctacg agcggctcgg    2160
cttcaccgtc accgccgacg tcgaggtgcc cgaaggaccg cgaacctggt gcatgacccg    2220
caagcccggt gcctgagttt aacgaaatga ccgaccaagc gacgcccaac ctgccatcac    2280
gatggccgca ataaaatatc tttattttca ttacatctgt gtgttggttt tttgtgtgga    2340
tcgatagcga taaggatcga tccgcgcatg gtgcactctc agtacaatct gctctgatgc    2400
cgcatagtta agccagcccc gacacccgcc aacacccgct gacgcgccct gacgggcttg    2460
tctgctcccg gcatccgctt acagacaagc tgtgaccgtc tccgggagct gcatgtgtca    2520
gaggttttca ccgtcatcac cgaaacgcgc gagacgaaag gcctcgtgta cgcctatt      2580 tttataggtt aatgtcatga taataatggt tcttagacg tcaggtggca cttttcgggg    2640
aaatgtgcgc ggaacccta tttgtttatt tttctaaata cattcaaata tgtatccgct    2700
catgagacaa taaccctgat aaatgcttca ataatattga aaaggaaga gtatgagtat    2760 tcaacatttc cgtgtcgccc ttattccctt ttttgcggca ttttgccttc ctgttttgc    2820 tcacccagaa acgctggtga agtaaaaga tgctgaagat cagttgggtg cacgagtggg    2880
ttacatcgaa ctggatctca acagcggtaa gatccttgag agttttcgcc ccgaagaccg    2940
ttttccaatg atgagcactt ttaaagttct gctatgtggc gcggtattat cccgtattga    3000
cgccgggcaa gagcaactcg gtcgccgcat acactattct cagaatgact tggttgagta    3060
ctcaccagtc acagaaaagc atcttacgga tggcatgaca gtaagagaat tatgcagtgc    3120
tgccataacc atgagtgata acactgcggc caacttactt ctgacaacga tcggaggacc    3180
gaaggagcta accgctttt tgcacaacat gggggatcat gtaactcgcc ttgatcgttg    3240
ggaaccggag ctgaatgaag ccataccaaa cgacgagcgt gacaccacga tgcctgtagc    3300
aatggcaaca acgttgcgca aactattaac tggcgaacta cttactctag cttcccggca    3360
acaattaata gactggatgg aggcggataa agttgcagga ccacttctgc gctcggccct    3420
tccggctggc tggtttattg ctgataaatc tggagccggt gagcgtgggt ctcgcggtat    3480
cattgcagca ctggggccag atggtaagcc ctcccgtatc gtagttatct acacgacggg    3540
gagtcaggca actatggatg aacgaaatag acagatcgct gagataggtg cctcactgat    3600
taagcattgg taactgtcag accaagttta ctcatatata ctttagattg atttaaaact    3660
tcatttttaa tttaaaagga tctaggtgaa gatcctttt gataatctca tgaccaaaat    3720
cccttaacgt gagttttcgt tccactgagc gtcagacccc gtagaaaaga tcaaaggatc    3780
ttcttgagat cctttttttc tgcgcgtaat ctgctgcttg caaacaaaaa aaccaccgct    3840 accagcggt gtttgtttgc cggatcaaga gctaccaact cttttccga aggtaactgg    3900 cttcagcaga gcgcagatac caaatactgt ccttctagtg tagccgtagt taggccacca    3960
cttcaagaac tctgtagcac cgcctacata cctcgctctg ctaatcctgt taccagtggc    4020
tgctgccagt ggcgataagt cgtgtcttac cgggttggac tcaagacgat agttaccgga    4080
taaggcgcag cggtcgggct gaacggggg ttcgtgcaca cagcccagct tggagcgaac    4140
gacctacacc gaactgagat acctacacg tgagcattga aaagcgcca cgcttcccga    4200 agggagaaag gcggacaggt atccggtaag cggcagggtc ggaacaggag agcgcacgag    4260
ggagcttcca gggggaaacg cctggtatct ttatagtcct gtcgggttc gccacctctg    4320 acttgagcgt cgatttttgt gatgctcgtc aggggggcgg agcctatgga aaaacgccag    4380
```

-continued

```
caacgcggcc ttttacggt tcctggcctt ttgctggcct tttgctcaca tgttctttcc    4440
tgcgttatcc cctgattctg tggataaccg tattaccgcc tttgagtgag ctgataccgc    4500
tcgccgcagc cgaacgaccg agcgcagcga gtcagtgagc gaggaagcgg aagagcgccc    4560
aatacgcaaa ccgcctctcc ccgcgcgttg gccgattcat taatgcagag cttgcaattc    4620
gcgcgttttt caatattatt gaagcattta tcagggttat tgtctcatga gcggatacat    4680
atttgaatgt atttagaaaa ataaacaaat aggggttccg cgcacatttc cccgaaaagt    4740
gccacctgac gtctaagaaa ccattattat catgacatta acctataaaa ataggcgtag    4800
tacgaggccc tttcactcat tagatgcatg tcgttacata acttacggta aatggcccgc    4860
ctggctgacc gcccaacgac ccccgcccat tgacgtcaat aatgacgtat gttcccatag    4920
taacgccaat agggactttc cattgacgtc aatgggtgga gtatttacgg taaactgccc    4980
acttggcagt acatcaagtg tatcatatgc caagtacgcc ccctattgac gtcaatgacg    5040
gtaaatggcc cgcctggcat tatgcccagt acatgacctt atgggacttt cctacttggc    5100
agtacatcta cgtattagtc atcgctatta ccatggtgat gcggttttgg cagtacatca    5160
atgggcgtgg atagcggttt gactcacggg gatttccaag tctccacccc attgacgtca    5220
atgggagttt gttttggcac caaaatcaac gggactttcc aaaatgtcgt aacaactccg    5280
ccccattgac gcaaatgggc ggtaggcgtg tacggtggga ggtctatata agcagagctc    5340
gtttagtgaa ccgtcagatc gcctggagac gccatcacg ctgttttgac ctccatagaa    5400
gacaccggga ccgatccagc ctccggactc tagcctaggc gcgaccat gtccggcttg    5460
aacgacatct tcgaggccca gaagatcgag tggcacgagg aaaagcttcg aaccatggtg    5520
agcaagggcg aggagctgtt caccggggtg gtgcccatcc tggtcgagct ggacggcgac    5580
gtaaacggcc acaagttcag cgtgtccggc gagggcgagg gcgatgccac ctacggcaag    5640
ctgaccctga agttcatctg caccaccggc aagctgcccg tgccctggcc caccctcgtg    5700
accaccctga cctacggcgt gcagtgcttc agccgctacc ccgaccacat gaagcagcac    5760
gacttcttca gtccgccat gcccgaaggc tacgtccagg agcgcaccat cttcttcaag    5820
gacgacggca actacaagac ccgcgccgag gtgaagttcg agggcgacac cctggtgaac    5880
cgcatcgagc tgaagggcat cgacttcaag gaggacggca acatcctggg gcacaagctg    5940
gagtacaact acaacagcca caacgtctat atcatggccg acaagcagaa gaacggcatc    6000
aaggtgaact tcaagatccg ccacaacatc gaggacggca gcgtgcagct cgccgaccac    6060
taccagcaga cacccccat cggcgacggc cccgtgctgc tgcccgacaa ccactacctg    6120
agcacccagt ccgccctgag caaagacccc aacgagaagc gcgatcacat ggtcctgctg    6180
gagttcgtga ccgccgccgg gatcactctc ggcatggacg agctgtacaa gtagctcgag    6240
tgcggcccca ataatgatt tattttgac tgatagtgac ctgttcgttg caacaaattg    6300
atgagcaatg ctttttata atgccaactt tgtacaaaaa agcaggctgc gatcgctcgg    6360
gcaggaagag ggcctatttc ccatgattcc ttcatatttg catatacgat acaaggctgt    6420
tagagagata attagaatta atttgactgt aaacacaaag atattagtac aaaatacgtg    6480
acgtagaaag taataatttc ttgggtagtt tgcagtttta aaattatgtt ttaaaatgga    6540
ctatcatatg cttaccgtaa cttgaaagta tttcgatttc ttggtttat atatcttgtg    6600
gaaaggacga ggatccgaca cctgctgcaa tagtgatcaa gagtcactat tgcagcaggt    6660
gtttttttg                                                            6669
```

<210> SEQ ID NO 8
<211> LENGTH: 6673
<212> TYPE: DNA
<213> ORGANISM: Artificial Sequence
<220> FEATURE:
<223> OTHER INFORMATION: human shTACE vector #1

<400> SEQUENCE: 8

| | | | | | |
|---|---|---|---|---|---|
| gaattcgcgg | ccctagcttg | ggatctttgt | gaaggaacct | tacttctgtg | gtgtgacata | 60 |
| attggacaaa | ctacctacag | agatttaaag | ctctaaggta | aatataaaat | ttttaagtgt | 120 |
| ataatgtgtt | aaactagctg | catatgcttg | ctgcttgaga | gttttgctta | ctgagtatga | 180 |
| tttatgaaaa | tattatacac | aggagctagt | gattctaatt | gtttgtgtat | tttagattca | 240 |
| cagtcccaag | gctcatttca | ggcccctcag | tcctcacagt | ctgttcatga | tcataatcag | 300 |
| ccataccaca | tttgtagagg | ttttacttgc | tttaaaaaac | ctcccacacc | tcccctgaa | 360 |
| cctgaaacat | aaaatgaatg | caattgttgt | tgttaacttg | tttattgcag | cttataatgg | 420 |
| ttacaaataa | agcaatagca | tcacaaattt | cacaaataaa | gcatttttt | cactgcattc | 480 |
| tagttgtggt | ttgtccaaac | tcatcaatgt | atcttatcat | gtctggatcg | atcctgcatt | 540 |
| aatgaatcgg | ccaacgcgcg | gggagaggcg | gtttgcgtat | tggctggcgt | aatagcgaag | 600 |
| aggcccgcac | cgatcgccct | tcccaacagt | tgcgcagcct | gaatggcgaa | tgggacgcgc | 660 |
| cctgtagcgg | cgcattaagc | gcggcgggtg | tggtggttac | gcgcagcgtg | accgctacac | 720 |
| ttgccagcgc | cctagcgccc | gctcctttcg | ctttcttccc | ttcctttctc | gccacgttcg | 780 |
| ccggctttcc | ccgtcaagct | ctaaatcggg | ggctcccttt | agggttccga | tttagtgctt | 840 |
| tacggcacct | cgaccccaaa | aaacttgatt | agggtgatgg | ttcacgtagt | gggccatcgc | 900 |
| cctgatagac | ggttttcgc | cctttgacgt | tggagtccac | gttctttaat | agtggactct | 960 |
| tgttccaaac | tggaacaaca | ctcaaccta | tctcggtcta | ttcttttgat | ttataaggga | 1020 |
| ttttgccgat | ttcggcctat | tggttaaaaa | atgagctgat | ttaacaaata | tttaacgcga | 1080 |
| attttaacaa | aatattaacg | tttacaattt | cgcctgatgc | ggtattttct | ccttacgcat | 1140 |
| ctgtgcggta | tttcacaccg | catacgcgga | tctgcgcagc | accatggcct | gaaataacct | 1200 |
| ctgaaagagg | aacttggtta | ggaaccttct | gaggcggaaa | gaaccagctg | tggaatgtgt | 1260 |
| gtcagttagg | gtgtggaaag | tccccaggct | ccccagcagg | cagaagtatg | caaagcatgc | 1320 |
| atctcaatta | gtcagcaacc | aggtgtggaa | agtcccagg | ctccccagca | ggcagaagta | 1380 |
| tgcaaagcat | gcatctcaat | tagtcagcaa | ccatagtccc | gcccctaact | ccgcccatcc | 1440 |
| cgcccctaac | tccgcccagt | tccgcccatt | ctccgcccca | tggctgacta | attttttta | 1500 |
| tttatgcaga | ggccgaggcc | gcctcggcct | ctgagctatt | ccagaagtag | tgaggaggct | 1560 |
| tttttggagg | cctaggcttt | tgcaaaaagc | ttgattcttc | tgacacaaca | gtctcgaact | 1620 |
| taaggctaga | gccaccatga | ccgagtacaa | gcccacggtg | cgcctcgcca | ccgcgacga | 1680 |
| cgtccccagg | gccgtacgca | ccctcgccgc | gcgttcgcc | gactacccg | ccacgcgcca | 1740 |
| caccgtcgat | ccggaccgcc | acatcgagcg | ggtcaccgag | ctgcaagaac | tcttcctcac | 1800 |
| gcgcgtcggg | ctcgacatcg | gcaaggtgtg | ggtcgcggac | gacggcgccg | cggtggcggt | 1860 |
| ctggaccacg | ccggagagcg | tcgaagcggg | ggcggtgttc | gccgagatcg | gcccgcgcat | 1920 |
| ggccgagttg | agcggttccc | ggctggccgc | gcagcaacag | atggaaggcc | tcctggcgcc | 1980 |
| gcaccggccc | aaggagcccg | cgtggttcct | ggccaccgtc | ggcgtctcgc | ccgaccacca | 2040 |
| gggcaagggt | ctgggcagcg | ccgtcgtgct | ccccggagtg | gaggcggccg | agcgcgccgg | 2100 |

```
ggtgcccgcc ttcctggaga cctccgcgcc ccgcaacctc cccttctacg agcggctcgg    2160
cttcaccgtc accgccgacg tcgaggtgcc cgaaggaccg cgaacctggt gcatgacccg    2220
caagcccggt gcctgagttt aacgaaatga ccgaccaagc gacgcccaac ctgccatcac    2280
gatggccgca ataaaatatc tttattttca ttacatctgt gtgttggttt tttgtgtgga    2340
tcgatagcga taaggatcga tccgcgcatg gtgcactctc agtacaatct gctctgatgc    2400
cgcatagtta agccagcccc gacacccgcc aacacccgct gacgcgccct gacgggcttg    2460
tctgctcccg gcatccgctt acagacaagc tgtgaccgtc tccgggagct gcatgtgtca    2520
gaggttttca ccgtcatcac cgaaacgcgc gagacgaaag gcctcgtga tacgcctatt     2580 tttataggtt aatgtcatga taataatggt ttcttagacg tcaggtggca cttttcgggg    2640
aaatgtgcgc ggaacccta tttgtttatt tttctaaata cattcaaata tgtatccgct     2700
catgagacaa taaccctgat aaatgcttca ataatattga aaaggaaga gtatgagtat     2760 tcaacatttc cgtgtcgccc ttattcccct ttttgcggca ttttgccttc ctgttttgc    2820 tcacccagaa acgctggtga agtaaaaga tgctgaagat cagttgggtg cacgagtggg    2880
ttacatcgaa ctggatctca acagcggtaa gatccttgag agttttcgcc ccgaagaccg    2940
ttttccaatg atgagcactt ttaaagttct gctatgtggc gcggtattat cccgtattga    3000
cgccgggcaa gagcaactcg gtcgccgcat acactattct cagaatgact tggttgagta    3060
ctcaccagtc acagaaaagc atcttacgga tggcatgaca gtaagagaat tatgcagtgc    3120
tgccataacc atgagtgata acactgcggc caacttactt ctgacaacga tcggaggacc    3180
gaaggagcta accgcttttt tgcacaacat gggggatcat gtaactcgcc ttgatcgttg    3240
ggaaccggag ctgaatgaag ccataccaaa cgacgagcgt gacaccacga tgcctgtagc    3300
aatggcaaca acgttgcgca aactattaac tggcgaacta cttactctag cttcccggca    3360
acaattaata gactggatgg aggcggataa agttgcagga ccacttctgc gctcggccct    3420
tccggctggc tggtttattg ctgataaatc tggagccggt gagcgtgggt ctcgcggtat    3480
cattgcagca ctggggccag atggtaagcc ctcccgtatc gtagttatct acacgacggg    3540
gagtcaggca actatggatg aacgaaatag acagatcgct gagataggtg cctcactgat    3600
taagcattgg taactgtcag accaagttta ctcatatata ctttagattg atttaaaact    3660 tcattttta tttaaaagga tctaggtgaa gatccttttt gataatctca tgaccaaaat    3720
cccttaacgt gagttttcgt tccactgagc gtcagacccc gtagaaaaga tcaaaggatc    3780
ttcttgagat cctttttttc tgcgcgtaat ctgctgcttg caaacaaaaa aaccaccgct    3840
accagcggtg gtttgtttgc cggatcaaga gctaccaact cttttccga aggtaactgg     3900 cttcagcaga gcgcagatac caaatactgt ccttctagtg tagccgtagt taggccacca    3960
cttcaagaac tctgtagcac cgcctacata cctcgctctg ctaatcctgt taccagtggc    4020
tgctgccagt ggcgataagt cgtgtcttac cgggttggac tcaagacgat agttaccgga    4080
taaggcgcag cggtcgggct gaacggggg ttcgtgcaca cagcccagct tggagcgaac     4140
gacctacacc gaactgagat acctacagcg tgagcattga gaaagcgcca cgcttcccga    4200
agggagaaag gcggacaggt atccggtaag cggcagggtc ggaacaggag agcgcacgag    4260
ggagcttcca gggggaaacg cctggtatct ttatagtcct gtcgggtttc gccacctctg    4320
acttgagcgt cgatttttgt gatgctcgtc aggggggcgg agcctatgga aaaacgccag    4380
caacgcggcc tttttacggt tcctggcctt ttgctggcct tttgctcaca tgttctttcc    4440
tgcgttatcc cctgattctg tggataaccg tattaccgcc tttgagtgag ctgataccgc    4500
```

-continued

```
tcgccgcagc cgaacgaccg agcgcagcga gtcagtgagc gaggaagcgg aagagcgccc    4560
aatacgcaaa ccgcctctcc ccgcgcgttg gccgattcat taatgcagag cttgcaattc    4620
gcgcgttttt caatattatt gaagcattta tcagggttat tgtctcatga gcggatacat    4680
atttgaatgt atttagaaaa ataaacaaat aggggttccg cgcacatttc cccgaaaagt    4740
gccacctgac gtctaagaaa ccattattat catgacatta acctataaaa ataggcgtag    4800
tacgaggccc tttcactcat tagatgcatg tcgttacata acttacggta aatggcccgc    4860
ctggctgacc gcccaacgac ccccgcccat tgacgtcaat aatgacgtat gttcccatag    4920
taacgccaat agggactttc cattgacgtc aatgggtgga gtatttacgg taaactgccc    4980
acttggcagt acatcaagtg tatcatatgc caagtacgcc ccctattgac gtcaatgacg    5040
gtaaatggcc cgcctggcat tatgcccagt acatgacctt atgggacttt cctacttggc    5100
agtacatcta cgtattagtc atcgctatta ccatggtgat gcggttttgg cagtacatca    5160
atgggcgtgg atagcggttt gactcacggg gatttccaag tctccacccc attgacgtca    5220
atgggagttt gttttggcac caaaatcaac gggactttcc aaaatgtcgt aacaactccg    5280
ccccattgac gcaaatgggc ggtaggcgtg tacggtggga ggtctatata agcagagctc    5340
gtttagtgaa ccgtcagatc gcctggagac gccatccacg ctgttttgac ctccatagaa    5400
gacaccggga ccgatccagc ctccggactc tagcctaggc gcggaccat gtccggcttg    5460 aacgacatct tcgaggccca agatcgag tggcacgagg aaaagcttcg aaccatggtg    5520
agcaagggcg aggagctgtt caccggggtg gtgcccatcc tggtcgagct ggacggcgac    5580
gtaaacggcc acaagttcag cgtgtccggc gagggcgagg gcgatgccac ctacggcaag    5640
ctgaccctga agttcatctg caccaccggc aagctgcccg tgccctggcc caccctcgtg    5700
accaccctga cctacggcgt gcagtgcttc agccgctacc ccgaccacat gaagcagcac    5760
gacttcttca gtccgccat gcccgaaggc tacgtccagg agcgcaccat cttcttcaag    5820
gacgacggca actacaagac ccgcgccgag gtgaagttcg agggcgacac cctggtgaac    5880
cgcatcgagc tgaagggcat cgacttcaag gaggacggca acatcctggg gcacaagctg    5940
gagtacaact acaacagcca caacgtctat atcatggccg acaagcagaa gaacggcatc    6000
aaggtgaact tcaagatccg ccacaacatc gaggacggca gcgtgcagct cgccgaccac    6060
taccagcaga acacccccat cggcgacggc ccgtgctgc tgcccgacaa ccactacctg    6120
agcacccagt ccgccctgag caaagacccc aacgagaagc gcgatcacat ggtcctgctg    6180
gagttcgtga ccgccgccgg gatcactctc ggcatggacg agctgtacaa gtagctcgag    6240
tgcggcccca ataatgatt ttatttgac tgatagtgac ctgttcgttg caacaaattg    6300
atgagcaatg ctttttata tgccaactt tgtacaaaaa agcaggctgc gatcgctcgg    6360
gcaggaagag ggcctatttc ccatgattcc ttcatatttg catatacgat acaaggctgt    6420
tagagagata attagaatta atttgactgt aaacacaaag atattagtac aaaatacgtg    6480
acgtagaaag taataatttc ttgggtagtt tgcagtttta aaattatgtt ttaaaatgga    6540
ctatcatatg cttaccgtaa cttgaaagta tttcgatttc ttggtttat atatcttgtg    6600 gaaaggacga ggatccggga gatttgttaa tgataccatc aagagtggta tcattaacaa    6660
atctcctttt ttg                                                        6673
```

<210> SEQ ID NO 9
<211> LENGTH: 6673
<212> TYPE: DNA

<213> ORGANISM: Artificial Sequence
<220> FEATURE:
<223> OTHER INFORMATION: human shTACE vector #2

<400> SEQUENCE: 9

```
gaattcgcgg ccctagcttg ggatctttgt gaaggaacct tacttctgtg gtgtgacata      60
attggacaaa ctacctacag agatttaaag ctctaaggta aatataaaat ttttaagtgt     120
ataatgtgtt aaactagctg catatgcttg ctgcttgaga gttttgctta ctgagtatga     180
tttatgaaaa tattatacac aggagctagt gattctaatt gtttgtgtat tttagattca     240
cagtcccaag gctcatttca ggcccctcag tcctcacagt ctgttcatga tcataatcag     300
ccataccaca tttgtagagg ttttacttgc tttaaaaaac ctcccacacc tcccctgaa      360
cctgaaacat aaaatgaatg caattgttgt tgttaacttg tttattgcag cttataatgg     420
ttacaaataa agcaatagca tcacaaattt cacaaataaa gcatttttt cactgcattc      480
tagttgtggt ttgtccaaac tcatcaatgt atcttatcat gtctggatcg atcctgcatt     540
aatgaatcgg ccaacgcgcg gggagaggcg gtttgcgtat tggctggcgt aatagcgaag     600
aggcccgcac cgatcgccct tcccaacagt tgcgcagcct gaatggcgaa tgggacgcgc     660
cctgtagcgg cgcattaagc gcggcgggtg tggtggttac gcgcagcgtg accgctacac     720
ttgccagcgc cctagcgccc gctcctttcg ctttcttccc ttcctttctc gccacgttcg     780
ccggctttcc ccgtcaagct ctaaatcggg gctccctttt agggttccga tttagtgctt     840
tacggcacct cgaccccaaa aaacttgatt agggtgatgg ttcacgtagt gggccatcgc     900
cctgatagac ggtttttcgc cctttgacgt tggagtccac gttctttaat agtggactct     960
tgttccaaac tggaacaaca ctcaacccta tctcggtcta ttcttttgat ttataaggga    1020
ttttgccgat ttcggcctat tggttaaaaa atgagctgat ttaacaaata tttaacgcga    1080
attttaacaa aatattaacg tttacaattt cgcctgatgc ggtattttct ccttacgcat    1140
ctgtgcggta tttcacaccg catacgcgga tctgcgcagc accatggcct gaaataacct    1200
ctgaaagagg aacttggtta ggaaccttct gaggcggaaa gaaccagctg tggaatgtgt    1260
gtcagttagg gtgtggaaag tccccaggct ccccagcagg cagaagtatg caaagcatgc    1320
atctcaatta gtcagcaacc aggtgtggaa agtccccagg ctccccagca ggcagaagta    1380
tgcaaagcat gcatctcaat tagtcagcaa ccatagtccc gcccctaact ccgcccatcc    1440
cgcccctaac tccgcccagt tccgcccatt ctccgcccca tggctgacta atttttttta    1500
tttatgcaga ggccgaggcc gcctcggcct ctgagctatt ccagaagtag tgaggaggct    1560
ttttggagg cctaggcttt tgcaaaaagc ttgattcttc tgacacaaca gtctcgaact    1620
taaggctaga gccaccatga ccgagtacaa gcccacggtg cgcctcgcca cccgcgacga    1680
cgtccccagg gccgtacgca ccctcgccgc cgcgttcgcc gactaccccg ccacgcgcca    1740
caccgtcgat ccggaccgcc acatcgagcg ggtcaccgag ctgcaagaac tcttcctcac    1800
gcgcgtcggg ctcgacatcg gcaaggtgtg gtcgcggac gacggcgccg cggtggcggt    1860
ctggaccacg ccggagagcg tcgaagcggg ggcggtgttc gccgagatcg cccgcgcat    1920
ggccgagttg agcggttccc ggctggccgc gcagcaacag atggaaggcc tcctggcgcc    1980
gcaccggccc aaggagcccg cgtggttcct ggccaccgtc ggcgtctcgc ccgaccacca    2040
gggcaagggt ctgggcagcg ccgtcgtgct cccggagtg gaggcggccg agcgcgccgg    2100
ggtgcccgcc ttcctggaga cctccgcgcc ccgcaacctc cccttctacg agcggctcgg    2160
cttcaccgtc accgccgacg tcgaggtgcc cgaaggaccg cgaacctggt gcatgacccg    2220
```

```
caagcccggt gcctgagttt aacgaaatga ccgaccaagc gacgcccaac ctgccatcac   2280
gatggccgca ataaaatatc tttatttca ttacatctgt gtgttggttt tttgtgtgga    2340
tcgatagcga taaggatcga tccgcgcatg gtgcactctc agtacaatct gctctgatgc   2400
cgcatagtta agccagcccc gacacccgcc aacacccgct gacgcgccct gacgggcttg   2460
tctgctcccg gcatccgctt acagacaagc tgtgaccgtc tccgggagct gcatgtgtca   2520
gaggttttca ccgtcatcac cgaaacgcgc gagacgaaag ggcctcgtga tacgcctatt   2580
tttataggtt aatgtcatga taataatggt tcttagacg tcaggtggca cttttcgggg    2640
aaatgtgcgc ggaaccccta tttgtttatt tttctaaata cattcaaata tgtatccgct   2700
catgagacaa taaccctgat aaatgcttca ataatattga aaaggaaga gtatgagtat    2760
tcaacatttc cgtgtcgccc ttattccctt ttttgcggca ttttgccttc ctgttttgc    2820
tcacccagaa acgctggtga agtaaaaga tgctgaagat cagttgggtg cacgagtggg    2880
ttacatcgaa ctggatctca acagcggtaa gatccttgag agttttcgcc ccgaagaccg   2940
ttttccaatg atgagcactt ttaaagttct gctatgtggc gcggtattat cccgtattga   3000
cgccgggcaa gagcaactcg gtcgccgcat acactattct cagaatgact tggttgagta   3060
ctcaccagtc acagaaaagc atcttacgga tggcatgaca gtaagagaat tatgcagtgc   3120
tgccataacc atgagtgata acactgcggc caacttactt ctgacaacga tcggaggacc   3180
gaaggagcta accgcttttt tgcacaacat gggggatcat gtaactcgcc ttgatcgttg   3240
ggaaccggag ctgaatgaag ccataccaaa cgacgagcgt gacaccacga tgcctgtagc   3300
aatggcaaca acgttgcgca aactattaac tggcgaacta cttactctag cttcccggca   3360
acaattaata gactggatgg aggcggataa agttgcagga ccacttctgc gctcggccct   3420
tccggctggc tggtttattg ctgataaatc tggagccggt gagcgtgggt ctcgcggtat   3480
cattgcagca ctggggccag atggtaagcc ctcccgtatc gtagttatct acacgacggg   3540
gagtcaggca actatggatg aacgaaatag acagatcgct gagataggtg cctcactgat   3600
taagcattgg taactgtcag accaagttta ctcatatata ctttagattg atttaaaact   3660
tcatttttaa tttaaaagga tctaggtgaa gatccttttt gataatctca tgaccaaaat   3720
cccttaacgt gagttttcgt tccactgagc gtcagacccc gtagaaaaga tcaaaggatc   3780
ttcttgagat cctttttttc tgcgcgtaat ctgctgcttg caaacaaaaa aaccaccgct   3840
accagcggtg gtttgtttgc cggatcaaga gctaccaact cttttccga aggtaactgg    3900
cttcagcaga gcgcagatac caaatactgt ccttctagtg tagccgtagt taggccacca   3960
cttcaagaac tctgtagcac cgcctacata cctcgctctg ctaatcctgt taccagtggc   4020
tgctgccagt ggcgataagt cgtgtcttac cgggttggac tcaagacgat agttaccgga   4080
taaggcgcag cggtcgggct gaacggggg ttcgtgcaca cagcccagct tggagcgaac    4140
gacctacacc gaactgagat acctacacgc tgagcattga aaagcgcca cgcttcccga    4200
agggagaaag gcggacaggt atccggtaag cggcagggtc ggaacaggag agcgcacgag   4260
ggagcttcca gggggaaacg cctggtatct ttatagtcct gtcgggtttc gccacctctg   4320
acttgagcgt cgatttttgt gatgctcgtc agggggggcgg agcctatgga aaaacgccag   4380
caacgcggcc ttttacggt tcctggcctt ttgctggcct tttgctcaca tgttctttcc    4440
tgcgttatcc cctgattctg tggataaccg tattaccgcc tttgagtgag ctgataccgc   4500
tcgccgcagc cgaacgaccg agcgcagcga gtcagtgagc gaggaagcgg aagagcgccc   4560
```

```
aatacgcaaa ccgcctctcc ccgcgcgttg gccgattcat taatgcagag cttgcaattc    4620
gcgcgttttt caatattatt gaagcattta tcagggttat tgtctcatga gcggatacat    4680
atttgaatgt atttagaaaa ataaacaaat aggggttccg cgcacatttc cccgaaaagt    4740
gccacctgac gtctaagaaa ccattattat catgacatta acctataaaa ataggcgtag    4800
tacgaggccc tttcactcat tagatgcatg tcgttacata acttacggta aatggcccgc    4860
ctggctgacc gcccaacgac ccccgcccat tgacgtcaat aatgacgtat gttcccatag    4920
taacgccaat agggactttc cattgacgtc aatgggtgga gtatttacgg taaactgccc    4980
acttggcagt acatcaagtg tatcatatgc caagtacgcc ccctattgac gtcaatgacg    5040
gtaaatggcc cgcctggcat tatgcccagt acatgacctt atgggacttt cctacttggc    5100
agtacatcta cgtattagtc atcgctatta ccatggtgat gcggttttgg cagtacatca    5160
atgggcgtgg atagcggttt gactcacggg gatttccaag tctccacccc attgacgtca    5220
atgggagttt gttttggcac caaaatcaac gggactttcc aaaatgtcgt aacaactccg    5280
ccccattgac gcaaatgggc ggtaggcgtg tacggtggga ggtctatata agcagagctc    5340
gtttagtgaa ccgtcagatc gcctggagac gccatccacg ctgttttgac ctccatagaa    5400
gacaccggga ccgatccagc ctccggactc tagcctaggc gcggaccat gtccggcttg    5460 aacgacatct tcgagcccca aagatcgag tggcacgagg aaaagcttcg aaccatggtg    5520
agcaagggcg aggagctgtt caccggggtg gtgcccatcc tggtcgagct ggacggcgac    5580
gtaaacggcc acaagttcag cgtgtccggc gagggcgagg gcgatgccac ctacggcaag    5640
ctgaccctga agttcatctg caccaccggc aagctgcccg tgccctggcc caccctcgtg    5700
accaccctga cctacggcgt gcagtgcttc agccgctacc ccgaccacat gaagcagcac    5760
gacttcttca gtccgccat gcccgaaggc tacgtccagg agcgcaccat cttcttcaag    5820
gacgacggca actacaagac ccgcgccgag gtgaagttcg agggcgacac cctggtgaac    5880
cgcatcgagc tgaagggcat cgacttcaag gaggacggca acatcctggg gcacaagctg    5940
gagtacaact acaacagcca caacgtctat atcatggccg acaagcagaa gaacggcatc    6000
aaggtgaact tcaagatccg ccacaacatc gaggacggca gcgtgcagct cgccgaccac    6060
taccagcaga acacccccat cggcgacggc cccgtgctgc tgcccgacaa ccactacctg    6120
agcacccagt ccgccctgag caaagacccc aacgagaagc gcgatcacat ggtcctgctg    6180
gagttcgtga ccgccgccgg gatcactctc ggcatggacg agctgtacaa gtagctcgag    6240
tgcggcccca ataatgatt ttattttgac tgatagtgac ctgttcgttg caacaaattg    6300
atgagcaatg ctttttttata atgccaactt tgtacaaaaa agcaggctgc gatcgctcgg    6360
gcaggaagag ggcctatttc ccatgattcc ttcatatttg catatacgat acaaggctgt    6420
tagagagata attagaatta atttgactgt aaacacaaag atattagtac aaaatacgtg    6480
acgtagaaag taataatttc ttgggtagtt tgcagtttta aaattatgtt ttaaatgga     6540 ctatcatatg cttaccgtaa cttgaaagta tttcgatttc ttggtttat atatcttgtg    6600 gaaaggacga ggatccgcct ggttacaact catgaatttc aagagaattc atgagttgta    6660
accaggtttt ttg                                                       6673
```

<210> SEQ ID NO 10
<211> LENGTH: 6673
<212> TYPE: DNA
<213> ORGANISM: Artificial Sequence
<220> FEATURE:
<223> OTHER INFORMATION: human shTACE vector #3

<400> SEQUENCE: 10

```
gaattcgcgg ccctagcttg ggatctttgt gaaggaacct tacttctgtg gtgtgacata      60
attggacaaa ctacctacag agatttaaag ctctaaggta aatataaaat ttttaagtgt     120
ataatgtgtt aaactagctg catatgcttg ctgcttgaga gttttgctta ctgagtatga     180
tttatgaaaa tattatacac aggagctagt gattctaatt gtttgtgtat tttagattca     240
cagtcccaag gctcatttca ggcccctcag tcctcacagt ctgttcatga tcataatcag     300
ccataccaca tttgtagagg ttttacttgc tttaaaaaac ctcccacacc tcccctgaa      360
cctgaaacat aaaatgaatg caattgttgt tgttaacttg tttattgcag cttataatgg     420
ttacaaataa agcaatagca tcacaaattt cacaaataaa gcattttttt cactgcattc     480
tagttgtggt ttgtccaaac tcatcaatgt atcttatcat gtctggatcg atcctgcatt     540
aatgaatcgg ccaacgcgcg gggagaggcg gtttgcgtat tgctggcgt aatagcgaag      600
aggcccgcac cgatcgccct tcccaacagt tgcgcagcct gaatggcgaa tgggacgcgc     660
cctgtagcgg cgcattaagc gcggcgggtg tggtggttac gcgcagcgtg accgctacac     720
ttgccagcgc cctagcgccc gctcctttcg ctttcttccc ttcctttctc gccacgttcg     780
ccggctttcc ccgtcaagct ctaaatcggg ggctcccttt agggttccga tttagtgctt     840
tacggcacct cgaccccaaa aaacttgatt agggtgatgg ttcacgtagt gggccatcgc     900
cctgatagac ggttttttcgc cctttgacgt tggagtccac gttctttaat agtggactct     960
tgttccaaac tggaacaaca ctcaacccta tctcggtcta ttcttttgat ttataaggga    1020
ttttgccgat ttcggcctat tggttaaaaa atgagctgat ttaacaaata tttaacgcga    1080
attttaacaa aatattaacg tttacaattt cgcctgatgc ggtatttctc ccttacgcat    1140
ctgtgcggta tttcacaccg catacgcgga tctgcgcagc accatggcct gaaataacct    1200
ctgaaagagg aacttggtta ggaaccttct gaggcggaaa gaaccagctg tggaatgtgt    1260
gtcagttagg gtgtggaaag tccccaggct ccccagcagg cagaagtatg caaagcatgc    1320
atctcaatta gtcagcaacc aggtgtggaa agtccccagg ctccccagca ggcagaagta    1380
tgcaaagcat gcatctcaat tagtcagcaa ccatagtccc gcccctaact ccgcccatcc    1440
cgcccctaac tccgcccagt tccgcccatt ctccgcccca tggctgacta atttttttta    1500
tttatgcaga ggccgaggcc gcctcggcct ctgagctatt ccagaagtag tgaggaggct    1560
tttttggagg cctaggcttt tgcaaaaagc ttgattcttc tgacacaaca gtctcgaact    1620
taaggctaga gccaccatga ccgagtacaa gcccacggtg cgcctcgcca cccgcgacga    1680
cgtccccagg gccgtacgca ccctcgccgc cgcgttcgcc gactaccccg ccacgcgcca    1740
caccgtcgat ccggaccgcc acatcgagcg ggtcaccgag ctgcaagaac tcttcctcac    1800
gcgcgtcggg ctcgacatcg gcaaggtgtg gtcgcggac gacggcgccg cggtggcggt    1860
ctggaccacg ccggagagcg tcgaagcggg ggcggtgttc gccgagatcg cccgcgcat    1920
ggccgagttg agcggttccc ggctggccgc gcagcaacag atggaaggcc tcctggcgcc    1980
gcaccggccc aaggagcccg cgtggttcct ggccaccgtc ggcgtctcgc ccgaccacca    2040
gggcaagggt ctgggcagcg ccgtcgtgct ccccggagtg gaggcggccg agcgcgccgg    2100
ggtgcccgcc ttcctggaga cctccgcgcc ccgcaacctc ccttctacg agcggctcgg    2160
cttcaccgtc accgccgacg tcgaggtgcc cgaaggaccg cgaacctggt gcatgacccg    2220
caagcccggt gcctgagttt aacgaaatga ccgaccaagc gacgcccaac ctgccatcac    2280
```

-continued

```
gatggccgca ataaaatatc tttattttca ttacatctgt gtgttggttt tttgtgtgga   2340
tcgatagcga taaggatcga tccgcgcatg gtgcactctc agtacaatct gctctgatgc   2400
cgcatagtta agccagcccc gacacccgcc aacacccgct gacgcgccct gacgggcttg   2460
tctgctcccg gcatccgctt acagacaagc tgtgaccgtc tccgggagct gcatgtgtca   2520
gaggttttca ccgtcatcac cgaaacgcgc gagacgaaag gcctcgtga tacgcctatt   2580 tttataggtt aatgtcatga taataatggt ttcttagacg tcaggtggca cttttcgggg   2640
aaatgtgcgc ggaacccta tttgtttatt tttctaaata cattcaaata tgtatccgct   2700
catgagacaa taaccctgat aaatgcttca ataatattga aaaggaaga gtatgagtat   2760 tcaacatttc cgtgtcgccc ttattccctt ttttgcggca ttttgccttc ctgttttgc    2820 tcacccagaa acgctggtga agtaaaaga tgctgaagat cagttgggtg cacgagtggg    2880
ttacatcgaa ctggatctca acagcggtaa gatccttgag agttttcgcc ccgaagaccg    2940
ttttccaatg atgagcactt ttaaagttct gctatgtggc gcggtattat cccgtattga    3000
cgccgggcaa gagcaactcg gtcgccgcat acactattct cagaatgact tggttgagta    3060
ctcaccagtc acagaaaagc atcttacgga tggcatgaca gtaagagaat tatgcagtgc    3120
tgccataacc atgagtgata acactgcggc caacttactt ctgacaacga tcggaggacc    3180
gaaggagcta accgcttttt tgcacaacat ggggatcat gtaactcgcc ttgatcgttg     3240
ggaaccggag ctgaatgaag ccataccaaa cgacgagcgt gacaccacga tgcctgtagc    3300
aatggcaaca acgttgcgca aactattaac tggcgaacta cttactctag cttcccggca    3360
acaattaata gactggatgg aggcggataa agttgcagga ccacttctgc gctcggccct    3420
tccggctggc tggtttattg ctgataaatc tggagccggt gagcgtgggt ctcgcggtat    3480
cattgcagca ctggggccag atggtaagcc ctcccgtatc gtagttatct acacgacggg    3540
gagtcaggca actatggatg aacgaaatag acagatcgct gagataggtg cctcactgat    3600
taagcattgg taactgtcag accaagttta ctcatatata ctttagattg atttaaaact    3660 tcattttttaa tttaaaagga tctaggtgaa gatcctttt gataatctca tgaccaaaat    3720
cccttaacgt gagttttcgt tccactgagc gtcagacccc gtagaaaaga tcaaaggatc    3780
ttcttgagat cctttttttc tgcgcgtaat ctgctgcttg caaacaaaaa aaccaccgct    3840
accagcggtg gtttgtttgc cggatcaaga gctaccaact cttttttccga aggtaactgg    3900 cttcagcaga gcgcagatac caaatactgt ccttctagtg tagccgtagt taggccacca    3960
cttcaagaac tctgtagcac cgcctacata cctcgctctg ctaatcctgt taccagtggc    4020
tgctgccagt ggcgataagt cgtgtcttac cgggttggac tcaagacgat agttaccgga    4080
taaggcgcag cggtcgggct gaacggggg ttcgtgcaca cagcccagct tggagcgaac    4140
gacctacacc gaactgagat acctacagcg tgagcattga gaaagcgcca cgcttcccga    4200
agggagaaag gcggacaggt atccggtaag cggcagggtc ggaacaggag agcgcacgag    4260
ggagcttcca gggggaaacg cctggtatct ttatagtcct gtcgggtttc gccacctctg    4320
acttgagcgt cgatttttgt gatgctcgtc aggggggcgg agcctatgga aaaacgccag    4380
caacgcggcc ttttacggt tcctggcctt ttgctggcct tttgctcaca tgttctttcc    4440
tgcgttatcc cctgattctg tggataaccg tattaccgcc tttgagtgag ctgataccgc    4500
tcgccgcagc cgaacgaccg agcgcagcga gtcagtgagc gaggaagcgg aagagcgccc    4560
aatacgcaaa ccgcctctcc ccgcgcgttg gccgattcat taatgcagag cttgcaattc    4620
gcgcgttttt caatattatt gaagcattta tcagggttat tgtctcatga gcggatacat    4680
```

```
atttgaatgt atttagaaaa ataaacaaat aggggttccg cgcacatttc cccgaaaagt    4740
gccacctgac gtctaagaaa ccattattat catgacatta acctataaaa ataggcgtag    4800
tacgaggccc tttcactcat tagatgcatg tcgttacata acttacggta aatggcccgc    4860
ctggctgacc gcccaacgac ccccgcccat tgacgtcaat aatgacgtat gttcccatag    4920
taacgccaat agggactttc cattgacgtc aatgggtgga gtatttacgg taaactgccc    4980
acttggcagt acatcaagtg tatcatatgc caagtacgcc ccctattgac gtcaatgacg    5040
gtaaatggcc cgcctggcat tatgcccagt acatgacctt atgggacttt cctacttggc    5100
agtacatcta cgtattagtc atcgctatta ccatggtgat gcggttttgg cagtacatca    5160
atgggcgtgg atagcggttt gactcacggg gatttccaag tctccacccc attgacgtca    5220
atgggagttt gttttggcac caaaatcaac gggactttcc aaaatgtcgt aacaactccg    5280
ccccattgac gcaaatgggc ggtaggcgtg tacggtggga ggtctatata agcagagctc    5340
gtttagtgaa ccgtcagatc gcctggagac gccatccacg ctgttttgac ctccatagaa    5400
gacaccggga ccgatccagc ctccggactc tagcctaggc gcgggaccat gtccggcttg    5460
aacgacatct tcgaggccca gaagatcgag tggcacgagg aaaagcttcg aaccatggtg    5520
agcaagggcg aggagctgtt caccggggtg gtgcccatcc tggtcgagct ggacggcgac    5580
gtaaacggcc acaagttcag cgtgtccggc gagggcgagg gcgatgccac ctacggcaag    5640
ctgaccctga agttcatctg caccaccggc aagctgcccg tgccctggcc caccctcgtg    5700
accaccctga cctacggcgt gcagtgcttc agccgctacc ccgaccacat gaagcagcac    5760
gacttcttca gtccgccat gcccgaaggc tacgtccagg agcgcaccat cttcttcaag    5820
gacgacggca actacaagac ccgcgccgag gtgaagttcg agggcgacac cctggtgaac    5880
cgcatcgagc tgaagggcat cgacttcaag gaggacggca acatcctggg gcacaagctg    5940
gagtacaact acaacagcca caacgtctat atcatggccg acaagcagaa gaacggcatc    6000
aaggtgaact tcaagatccg ccacaacatc gaggacggca gcgtgcagct cgccgaccac    6060
taccagcaga acacccccat cggcgacggc cccgtgctgc tgcccgacaa ccactacctg    6120
agcacccagt ccgccctgag caaagacccc aacgagaagc gcgatcacat ggtcctgctg    6180
gagttcgtga ccgccgccgg gatcactctc ggcatggacg agctgtacaa gtagctcgag    6240
tgcggcccca ataatgatt ttatttgac tgatagtgac ctgttcgttg caacaaattg    6300
atgagcaatg cttttttata atgccaactt tgtacaaaaa agcaggctgc gatcgctcgg    6360
gcaggaagag ggcctatttc ccatgattcc ttcatatttg catatacgat acaaggctgt    6420
tagagagata attagaatta atttgactgt aaacacaaag atattagtac aaaatacgtg    6480
acgtagaaag taataatttc ttgggtagtt tgcagtttta aaattatgtt ttaaaatgga    6540
ctatcatatg cttaccgtaa cttgaaagta tttcgatttc ttggttat atatcttgtg    6600 gaaaggacga ggatccgggc gattaatgct acttgcaatc aagagttgca agtagcatta    6660
atcgcctttt ttg                                                       6673
```

<210> SEQ ID NO 11
<211> LENGTH: 6673
<212> TYPE: DNA
<213> ORGANISM: Artificial Sequence
<220> FEATURE:
<223> OTHER INFORMATION: human shTACE vector #4

<400> SEQUENCE: 11

-continued

| | | | | | |
|---|---|---|---|---|---|
| gaattcgcgg | ccctagcttg | ggatctttgt | gaaggaacct | tacttctgtg | gtgtgacata | 60 |
| attggacaaa | ctacctacag | agatttaaag | ctctaaggta | aatataaaat | ttttaagtgt | 120 |
| ataatgtgtt | aaactagctg | catatgcttg | ctgcttgaga | gttttgctta | ctgagtatga | 180 |
| tttatgaaaa | tattatacac | aggagctagt | gattctaatt | gtttgtgtat | tttagattca | 240 |
| cagtcccaag | gctcatttca | ggcccctcag | tcctcacagt | ctgttcatga | tcataatcag | 300 |
| ccataccaca | tttgtagagg | ttttacttgc | tttaaaaaac | ctcccacacc | tcccctgaa | 360 |
| cctgaaacat | aaaatgaatg | caattgttgt | tgttaacttg | tttattgcag | cttataatgg | 420 |
| ttacaaataa | agcaatagca | tcacaaattt | cacaaataaa | gcattttttt | cactgcattc | 480 |
| tagttgtggt | ttgtccaaac | tcatcaatgt | atcttatcat | gtctggatcg | atcctgcatt | 540 |
| aatgaatcgg | ccaacgcgcg | gggagaggcg | gtttgcgtat | tgggctggcgt | aatagcgaag | 600 |
| aggcccgcac | cgatcgccct | tcccaacagt | tgcgcagcct | gaatggcgaa | tgggacgcgc | 660 |
| cctgtagcgg | cgcattaagc | gcggcgggtg | tggtggttac | gcgcagcgtg | accgctacac | 720 |
| ttgccagcgc | cctagcgccc | gctcctttcg | ctttcttccc | ttcctttctc | gccacgttcg | 780 |
| ccggctttcc | ccgtcaagct | ctaaatcggg | ggctcccttt | agggttccga | tttagtgctt | 840 |
| tacggcacct | cgaccccaaa | aaacttgatt | agggtgatgg | ttcacgtagt | gggccatcgc | 900 |
| cctgatagac | ggtttttcgc | cctttgacgt | tggagtccac | gttctttaat | agtggactct | 960 |
| tgttccaaac | tggaacaaca | ctcaaccc ta | tctcggtcta | ttcttttgat | ttataaggga | 1020 |
| ttttgccgat | ttcggcctat | tggttaaaaa | atgagctgat | ttaacaaata | tttaacgcga | 1080 |
| attttaacaa | aatattaacg | tttacaattt | cgcctgatgc | ggtattttct | ccttacgcat | 1140 |
| ctgtgcggta | tttcacaccg | catacgcgga | tctgcgcagc | accatggcct | gaaataacct | 1200 |
| ctgaaagagg | aacttggtta | ggaaccttct | gaggcggaaa | gaaccagctg | tggaatgtgt | 1260 |
| gtcagttagg | gtgtggaaag | tccccaggct | ccccagcagg | cagaagtatg | caaagcatgc | 1320 |
| atctcaatta | gtcagcaacc | aggtgtggaa | agtcccagg | ctccccagca | ggcagaagta | 1380 |
| tgcaaagcat | gcatctcaat | tagtcagcaa | ccatagtccc | gcccctaact | ccgcccatcc | 1440 |
| cgcccctaac | tccgcccagt | tccgcccatt | ctccgcccca | tggctgacta | attttttta | 1500 |
| tttatgcaga | ggccgaggcc | gcctcggcct | ctgagctatt | ccagaagtag | tgaggaggct | 1560 |
| ttttggagg | cctaggcttt | tgcaaaaagc | ttgattcttc | tgacacaaca | gtctcgaact | 1620 |
| taaggctaga | gccaccatga | ccgagtacaa | gcccacggtg | cgcctcgcca | cccgcgacga | 1680 |
| cgtccccagg | gccgtacgca | ccctcgccgc | gcgttcgcc | gactaccccg | ccacgcgcca | 1740 |
| caccgtcgat | ccggaccgcc | acatcgagcg | ggtcaccgag | ctgcaagaac | tcttcctcac | 1800 |
| gcgcgtcggg | ctcgacatcg | gcaaggtgtg | ggtcgcggac | gacggcgccg | cggtggcggt | 1860 |
| ctggaccacg | ccggagagcg | tcgaagcggg | ggcggtgttc | gccgagatcg | gcccgcgcat | 1920 |
| ggccgagttg | agcggttccc | ggctggccgc | gcagcaacag | atggaaggcc | tcctggcgcc | 1980 |
| gcaccggccc | aaggagcccg | cgtggttcct | ggccaccgtc | ggcgtctcgc | ccgaccacca | 2040 |
| gggcaagggt | ctgggcagcg | ccgtcgtgct | ccccggagtg | gaggcggccg | agcgcgccgg | 2100 |
| ggtgcccgcc | ttcctggaga | cctccgcgcc | ccgcaacctc | cccttctacg | agcggctcgg | 2160 |
| cttcaccgtc | accgccgacg | tcgaggtgcc | cgaaggaccg | cgaacctggt | gcatgacccg | 2220 |
| caagcccggt | gcctgagttt | aacgaaatga | ccgaccaagc | gacgcccaac | ctgccatcac | 2280 |
| gatgccgcca | ataaaaatatc | tttattttca | ttacatctgt | gtgttggttt | tttgtgtgga | 2340 |
| tcgatagcga | taaggatcga | tccgcgcatg | gtgcactctc | agtacaatct | gctctgatgc | 2400 |

```
cgcatagtta agccagcccc gacacccgcc aacacccgct gacgcgccct gacgggcttg    2460
tctgctcccg gcatccgctt acagacaagc tgtgaccgtc tccgggagct gcatgtgtca    2520
gaggttttca ccgtcatcac cgaaacgcgc gagacgaaag ggcctcgtga tacgcctatt    2580
tttataggtt aatgtcatga taataatggt ttcttagacg tcaggtggca cttttcgggg    2640
aaatgtgcgc ggaaccccta tttgtttatt tttctaaata cattcaaata tgtatccgct    2700
catgagacaa taaccctgat aaatgcttca ataatattga aaaggaaga gtatgagtat    2760 tcaacatttc cgtgtcgccc ttattccctt ttttgcggca ttttgccttc ctgttttgc    2820 tcacccagaa acgctggtga agtaaaaga tgctgaagat cagttgggtg cacgagtggg    2880
ttacatcgaa ctggatctca acagcggtaa gatccttgag agttttcgcc ccgaagaccg    2940
ttttccaatg atgagcactt ttaaagttct gctatgtggc gcggtattat cccgtattga    3000
cgccgggcaa gagcaactcg gtcgccgcat acactattct cagaatgact tggttgagta    3060
ctcaccagtc acagaaaagc atcttacgga tggcatgaca gtaagagaat tatgcagtgc    3120
tgccataacc atgagtgata acactgcggc caacttactt ctgacaacga tcggaggacc    3180
gaaggagcta accgcttttt tgcacaacat gggggatcat gtaactcgcc ttgatcgttg    3240
ggaaccggag ctgaatgaag ccataccaaa cgacgagcgt gacaccacga tgcctgtagc    3300
aatggcaaca acgttgcgca aactattaac tggcgaacta cttactctag cttcccggca    3360
acaattaata gactggatgg aggcggataa agttgcagga ccacttctgc gctcggccct    3420
tccggctggc tggtttattg ctgataaatc tggagccggt gagcgtgggt ctcgcggtat    3480
cattgcagca ctggggccag atggtaagcc ctcccgtatc gtagttatct acacgacggg    3540
gagtcaggca actatggatg aacgaaatag acagatcgct gagataggtg cctcactgat    3600
taagcattgg taactgtcag accaagttta ctcatatata ctttagattg atttaaaact    3660 tcattttta tttaaaagga tctaggtgaa gatcctttt gataatctca tgaccaaaat    3720
cccttaacgt gagttttcgt tccactgagc gtcagacccc gtagaaaaga tcaaaggatc    3780
ttcttgagat cctttttttc tgcgcgtaat ctgctgcttg caaacaaaaa aaccaccgct    3840
accagcggtg gtttgtttgc cggatcaaga gctaccaact cttttccga aggtaactgg    3900 cttcagcaga gcgcagatac caaatactgt ccttctagtg tagccgtagt taggccacca    3960
cttcaagaac tctgtagcac cgcctacata cctcgctctg ctaatcctgt taccagtggc    4020
tgctgccagt ggcgataagt cgtgtcttac cgggttggac tcaagacgat agttaccgga    4080
taaggcgcag cggtcgggct gaacgggggg ttcgtgcaca cagcccagct tggagcgaac    4140
gacctacacc gaactgagat acctacagcg tgagcattga gaaagcgcca cgcttcccga    4200
agggagaaag gcggacaggt atccggtaag cggcagggtc ggaacaggag agcgcacgag    4260
ggagcttcca gggggaaacg cctggtatct ttatagtcct gtcgggtttc gccacctctg    4320
acttgagcgt cgatttttgt gatgctcgtc aggggggcgg agcctatgga aaaacgccag    4380
caacgcggcc ttttacggt tcctggcctt ttgctggcct tttgctcaca tgttctttcc    4440
tgcgttatcc cctgattctg tggataaccg tattaccgcc tttgagtgag ctgataccgc    4500
tcgccgcagc cgaacgaccg agcgcagcga gtcagtgagc gaggaagcgg aagagcgccc    4560
aatacgcaaa ccgcctctcc ccgcgcgttg gccgattcat taatgcagag cttgcaattc    4620
gcgcgttttt caatattatt gaagcattta tcagggttat tgtctcatga gcggatacat    4680
atttgaatgt atttagaaaa ataaacaaat aggggttccg cgcacatttc cccgaaaagt    4740
```

```
gccacctgac gtctaagaaa ccattattat catgacatta acctataaaa ataggcgtag    4800
tacgaggccc tttcactcat tagatgcatg tcgttacata acttacggta aatggcccgc    4860
ctggctgacc gcccaacgac ccccgcccat tgacgtcaat aatgacgtat gttcccatag    4920
taacgccaat agggactttc cattgacgtc aatgggtgga gtatttacgg taaactgccc    4980
acttggcagt acatcaagtg tatcatatgc caagtacgcc ccctattgac gtcaatgacg    5040
gtaaatggcc cgcctggcat tatgcccagt acatgacctt atgggacttt cctacttggc    5100
agtacatcta cgtattagtc atcgctatta ccatggtgat gcggttttgg cagtacatca    5160
atgggcgtgg atagcggttt gactcacggg gatttccaag tctccacccc attgacgtca    5220
atgggagttt gttttggcac caaaatcaac gggactttcc aaaatgtcgt aacaactccg    5280
ccccattgac gcaaatgggc ggtaggcgtg tacggtggga ggtctatata agcagagctc    5340
gtttagtgaa ccgtcagatc gcctggagac gccatccacg ctgttttgac ctccatagaa    5400
gacaccggga ccgatccagc ctccggactc tagcctaggc gcggaccat gtccggcttg     5460
aacgacatct tcgaggccca agatcgag tggcacgagg aaaagcttcg aaccatggtg     5520
agcaagggcg aggagctgtt caccggggtg gtgcccatcc tggtcgagct ggacggcgac    5580
gtaaacggcc acaagttcag cgtgtccggc gagggcgagg gcgatgccac ctacggcaag    5640
ctgaccctga agttcatctg caccaccggc aagctgcccg tgccctggcc caccctcgtg    5700
accaccctga cctacggcgt gcagtgcttc agccgctacc ccgaccacat gaagcagcac    5760
gacttcttca gtccgccat gcccgaaggc tacgtccagg agcgcaccat cttcttcaag    5820
gacgacggca actacaagac ccgcgccgag gtgaagttcg agggcgacac cctggtgaac    5880
cgcatcgagc tgaagggcat cgacttcaag gaggacggca acatcctggg gcacaagctg    5940
gagtacaact acaacagcca caacgtctat atcatggccg acaagcagaa gaacggcatc    6000
aaggtgaact tcaagatccg ccacaacatc gaggacggca gcgtgcagct cgccgaccac    6060
taccagcaga acacccccat cggcgacggc cccgtgctgc tgcccgacaa ccactacctg    6120
agcacccagt ccgccctgag caaagacccc aacgagaagc gcgatcacat ggtcctgctg    6180
gagttcgtga ccgccgccgg gatcactctc ggcatggacg agctgtacaa gtagctcgag    6240
tgcggcccca ataatgatt ttatttttgac tgatagtgac ctgttcgttg caacaaattg     6300
atgagcaatg cttttttata atgccaactt tgtacaaaaa agcaggctgc gatcgctcgg    6360
gcaggaagag ggcctatttc ccatgattcc ttcatatttg catatacgat acaaggctgt    6420
tagagagata attagaatta atttgactgt aaacacaaag atattagtac aaaatacgtg    6480
acgtagaaag taataatttc ttgggtagtt tgcagtttta aaattatgtt ttaaaatgga    6540
ctatcatatg cttaccgtaa cttgaaagta tttcgatttc ttggtttat atatcttgtg    6600
gaaaggacga ggatccgcca ttgtgtggat aagaaatttc aagagaattt cttatccaca    6660
caatggtttt ttg                                                       6673
```

<210> SEQ ID NO 12
<211> LENGTH: 20
<212> TYPE: DNA
<213> ORGANISM: Artificial Sequence
<220> FEATURE:
<223> OTHER INFORMATION: Forward primer for TACE

<400> SEQUENCE: 12

```
gtacgtcgat gcagagcaaa                                                  20
```

```
<210> SEQ ID NO 13
<211> LENGTH: 20
<212> TYPE: DNA
<213> ORGANISM: Artificial Sequence
<220> FEATURE:
<223> OTHER INFORMATION: Reverse primer for TACE

<400> SEQUENCE: 13
aaaccagaac agacccaacg                                          20

<210> SEQ ID NO 14
<211> LENGTH: 9
<212> TYPE: PRT
<213> ORGANISM: Artificial Sequence
<220> FEATURE:
<223> OTHER INFORMATION: 9-arginine sequences

<400> SEQUENCE: 14

Arg Arg Arg Arg Arg Arg Arg Arg Arg
1               5

<210> SEQ ID NO 15
<211> LENGTH: 18
<212> TYPE: PRT
<213> ORGANISM: Artificial Sequence
<220> FEATURE:
<223> OTHER INFORMATION: ATS-R9

<400> SEQUENCE: 15

Cys Lys Gly Gly Arg Ala Lys Asp Arg Arg Arg Arg Arg Arg
1               5                   10                  15

Arg Cys
```